United States Patent [19]
Odell et al.

[11] Patent Number: 5,658,772
[45] Date of Patent: *Aug. 19, 1997

[54] SITE-SPECIFIC RECOMBINATION OF DNA IN PLANT CELLS

[75] Inventors: Joan Tellefsen Odell, Wilmington, Del.; Sandra Hoff Russell, Avondale, Pa.; Brian Lee Sauer, Bethesda, Md.; Francis Chuoh Hsu, Newark, Del.; Jennie Bih-Jien Shen, Wilmington, Del.

[73] Assignee: E. I. Du Pont de Nemours and Company, Wilmington, Del.

[*] Notice: The portion of the term of this patent subsequent to Feb. 19, 2011, has been disclaimed.

[21] Appl. No.: 281,714

[22] Filed: Jul. 27, 1994

Related U.S. Application Data

[63] Continuation-in-part of Ser. No. 861,802, filed as PCT/US90/07295, Dec. 19, 1990, abandoned, which is a continuation-in-part of Ser. No. 455,221, Dec. 22, 1989, abandoned.

[51] Int. Cl.$^6$ .................. C12N 15/82; C12N 15/52; C12N 5/10; A01H 5/00
[52] U.S. Cl. .................. 435/172.3; 435/69.1; 435/172.1; 435/320.1; 435/418; 435/419; 435/410; 536/23.74; 800/205; 935/34
[58] Field of Search ................ 435/172.1, 172.3, 435/240.4, 320.1, 69.1; 800/205; 935/34; 536/23.74

[56] References Cited

U.S. PATENT DOCUMENTS

| | | | |
|---|---|---|---|
| 4,956,282 | 9/1990 | Goodman et al. | 435/69.51 |
| 4,959,317 | 9/1990 | Sauer | 435/69.1 |
| 4,962,028 | 10/1990 | Bedbrook et al. | 435/172.3 |
| 5,007,198 | 4/1991 | Gray et al. | 47/58 |

FOREIGN PATENT DOCUMENTS

| | | | |
|---|---|---|---|
| 0 220 009 | 4/1987 | European Pat. Off. | C12N 15/00 |
| WO 91/03472 | 3/1991 | WIPO | C07D 317/42 |
| WO 91/04332 | 4/1991 | WIPO | C12N 15/82 |

OTHER PUBLICATIONS

Dale et al 1991 (Dec 1) Proc Natl Acad Sci USA 88:10558–10562.
Qin et al 1994(Mar. 1) Proc Natl Acad Sci USA 91:1706–1710.
Bayley et al 1992 (Jan) Pl. Molec Biol 18:353–361.
Russell et al 1992 (Jul.) Mol Genet Genet 234:49–59.
Dale et al 1992 (Apr.) J of Cell Biochem 16F: 206 (Abstract #Y108).
Qin et al 1992 (Apr.) J of Cell Biochem 16F:210 (Abstract #Y125).
Odell et al 1994 (Oct.) Pl Physiol 106:447–458.
Ambremski, K. et al, *Cell,* 32, 1301–1311 (1983).
Sauer, B., *Molecular and Cellular Biology,* 7, 2087–2096 (1987).
Sauer, B. et al, *Proc. Natl. Acad. Sci. USA,* 85, 5166–5170 (1988).
Sauer, B. et al *Nucl. Acids Res.,* 17, 147–161 (1989).
Gatz, C., et al *Proc. Natl. Acad. Sci. USA,* 85, 1394–1397 (1988).
Baker, B. et al, *Proc. Natl. Acad. Sci. USA,* 83, 4844–4848 (1986).
Lassner, M.W. et al, *Mol. Gen. Genet.,* 218, 25–32 (1989).
Paszkoski, J. et al, 7(13), 4021–4026 (1988).
Perani, L. et al, *Physiol. Plantarum,* 68, 566–570 (1986).
Harpster, M.H. et al, *Mol. Gen. Genet.,* 212, 182–190 (1988).
Dale, E.C. et al, *Gene,* 91, 79–85 (1990).
Odell, J. et al, *Mol. Gen. Genet.,* 223, 369–378 (1990).
Sauer, B. et al, *Proc. Nat'l. Acad. Sci. USA,* 84, 9108–9112 (1987).
Backman, K. et al, *Bio. Technology,* Dec. 1984.
Langeveld, S.A. et al, *Mol. Gen. Genet.,* 199, 396–400 (1985).
Barnes, G. et al, *Proc. Nat'l. Acad. Sci.,* 82, 1354–1358 (1985).
Brent, R. et al, *Nature,* 312, 612–615 (1984).
McInnes, E. et al, *Plant Cell Reports,* 9, 647–650 (1991).
Wolfe, D.W., *American Vegetable Grower,* 60–61 (1990).
Sarmento, G.G. et al, *J. Cell. Biochem.,* Suppl. 13D, Abstract No. M150, p. 268 (1989).
Moore, J. *American Vegetable Grower,* 39–40 (1990).
Srivastava, D.K. et al, *Plant Cell Reports,* 8, 300–302 (1989).
Simon, J.E. et al, *American Vegetable Grower,* 17–19 (1992).
Amselem, et al, *Plant Molecular Biology,* 19, 421–432 (1992).
Malepszy, S. et al,. *Pflanzenphysiol. Bd.,* 111, S273–S276 (1983).
Dong, J. et al, *Plant Cell Reports,* 9, 559–562 (1991).
Compton, M.E. et al, *Plant Cell Reports,* 12, 61–65 (1993).
Maynard, D.N., *Citrus and Vegetable Magazine,* 77–79 (1989).
Fang, G. et al, *Plant Cell Reports,* 160–164 (1990).
Dong, J. et al, *Bio/Technology,* 9, 858–863 (1991).
Czako, M. et al, *Mol. Gen. Genet.,* 235, 33–40 (1992).
Katavic, *Plant Cell, Tissue and Organ Culture,* 24, 35–42 (1991).

*Primary Examiner*—Patricia R. Moody

[57] ABSTRACT

A method for producing site-specific recombination of DNA in plant cells. A first DNA sequence comprising a first lox site and a second DNA sequence comprising a second lox site are introduced into the cells. The lox sites are contacted with Cre to produce recombination. Also disclosed are related plasmids, transformed plant cells, and plants containing the transformed cells.

39 Claims, 9 Drawing Sheets

5'-Untranslated leader sequence in WM403 transcript/ coding sequence:
+1UACAAGAAGAAAAGAAGAUAGAAAAACCAAAGCAAGAGAAG/AUG 5'-Untranslated leader sequence in JS77 & JS96/ GUS coding sequence:
+1UACAAGAAGAAAAGAAGAUAGAAAAACCAAAGCAAGAGA<u>CC</u>/AUG

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 2726 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

```
GGATCTTTTT AAGTGTTGGG GCTGGTTTTT ATTTTGTTTA CGAGTTTCAA AATGTTACCT      60

AATTTAGTAT TTCAGTTTCA AAATATTACA ATTTTACTAT TTAAATTTGA ATTTTGTTTT     120

AAATGGTCA CTAGGTTTCA ACGTTTTATA TTTTTAACCT TAATTTTTCA TTAAATACTC     180

ATCTTCAATC GTTGACGTTA ATGTCTATTA ATTAATTAAA ATTAATTATA AAGTGAGATT     240

TCAAAAGTGA TGAAAATCTG TGAAACTTAA TTAATTATAG TTTTTTTAAT TAATTTAAAT     300

TTATTAACAT ACATTAACAT TGAAAATGAA AAAATGAATA TTTAGTAAAA AATCGAGGTT     360
```

```
AAATGTGTAA ATATTGAAAC TTGGGGACCA AATTAAAATA AAGCTCAAAT GTCAATTCAT    420
AACAAAGTTC AAATGAATTT CGTTGTTTGT TATGGTAGGA AAGAGAATAA CTTTAAAATA    480
CGAAATGATT TCAAATCCTG TTTTTACTTT AAAAAAACCT TCCCAACCAA AATGCTCGGA    540
TTTTGCAGAA TTTCATAGGA TTTAAAAATA AATTACCTAG TCGACCTTGT CATATTCTAA    600
TTTTCAATTA ACAGTAAATT TTAACTTTT TTTTTCTCT TTTTCTGTTA ACATCCAAAC     660
ACAATTTTAA ATACATTCAT TCAAATCTTT CTCGTTCCAA ATAAATAAT TAATTTAAA     720
TCATTTTTA AATTTCAAAT TACAAAATTT AAAATCATTT GTTCAAATTT GTTAAATCTA    780
TATTTAGGGT AAAAATTCTA AAAGTTACCG AAAGTTGAGC AAACCATTTT GTTGTCTCCT    840
TTCTTATATT AGTCCACCTT TTTGTTTGAA AGACATTTAT GCAATTCACG AAATAATTAA    900
ATTAGAAATC CAACTAAGAT CTACGTTGAT GCAATTTTGA ACTTACCTTG TTCGGGTCCA    960
CCACATTGTA TTATTAAAAA ACAAATTAAG AACATCTTGG TATATGAACA ATTCGAGTAC   1020
TCACTTCAAG ATGAGATACA ACAATTACCT ATAAGTTATA CTAATTTAAA AAGTGGTCCC   1080
AATTCATAAC TTTGTTTGTT GTTTAATTTC CGTAATCATA ATGAATTGTA GGACCCGCTT   1140
GTAAATCTGT AATCAAAACG CGTAATTTGA TTGAAGAACG AAGGATGTTC AATCTAATTG   1200
TAGTTGAAAA TTGTGTGAGA TCCACTACAT TTACCGTTAG TGTTATAGAT ATTGTTGCTA   1260
TAACGGTACG AATGTTATGA ATCTGTCACA TTTATTTTTT ACGTTATTA TTACCATTCG    1320
GGTTAAACAG TAACGGTGAC GATAACGATA ATAATAAAAT GTGACAAATT CATAATTTA    1380
AGTAAACGTG ATCAAAAGTA ATCCAATTAC ATGTTGGAAT GCCTTGAATC ATAACCTAAT   1440
TAAAATTGGT ATCTTATATA TTTAATTATT TAATTTTTTT CCTTCTCCAC TTAGGGTTTA   1500
AAAAGTGCAC TATATAAACT CTTTAATTCT ATAGACTTTA TTCATTTGT GGTATTATAT    1560
AATTTTATAA CATTCTCTCT AATAAAATTG TTATCCCTCT ATCTCGTGGA CGTAACTAAC   1620
ACATTGTTAG TGCACAACGT AAATTTGTGT GTCGATCTTT ATTTCTATTT TTACGTTAT    1680
TTTGTATTAT TTAATTGTCG ATTTCATAAC ATTATATTTG TGATTCAGAC CCATTACGAT   1740
TGGACCATCA ATGAAATCTC ATTACGATTA CATCAATTTT TATTACGAAT TGGTAAATGT   1800
AAATATTTTA ATGCTCCTTT GGGACAAAAA AAAAAAATT ATTTAACTC CTTCATGTAA     1860
TCAACAAGAC AGAATAATAT TAAATGTGAA TTTATATTTG GGTGATTGCT AAGATTTAGC   1920
AATTTCTCTA AAACCAAAAG AACCTCAAAC CATATCAATA CACAATAGAA GTATATGGGG   1980
CCATGCAAAT TTAAAGGCCA ATGAATTGCT GATGGGCCAC TCAACTACTT GTTTCTATTA   2040
GAACAAAGAT TCCCATGCAG AAACTCATAA ATTACTCCAT GCAAAAGAC TACCAAAATT    2100
CCCTTTGCTA GCTATAAATT TGGAGGCCTC AAACCATTTT CACTACAAGA AGAAAGAAG    2160
ATAGAAAAC CAAAGCAAGA GAAGATGAAA ATCGTCGGTA AGGTTCTCGT CGCCATGCTC    2220
GTAATCTCTG CAATAGCAAT GGCGCTTCTG GAAAATGTTG AAGGAGGAAG AGAGATGGGT   2280
TTGAAGGAAG CAACTGCAAA TGCTTATCCC CATGTTTTAA ATGAAAAATA TGAGGGATAC   2340
AAACCCAAGG AAGACTATGA GTGTGATGGA TACAAATATA AAGATAAAAA TTGCTATGAA   2400
TATGGCAATT GTGACAAATC TCCCTACAAC GAAGAAGAAG ACGACCGTCA ATACAACGGG   2460
AGTCCGTATA AGAAACCGAT ACCGAAGCCG AAAGAGATGG CCAGAAAGTA TGGAGTTCAC   2520
CACAATTTCC CTTGAAACTA AAGCTAACCC ATAAGCATAG TTATATATTG CTTATGTTTT   2580
CTATGAATAA TAATAATAAG TAGGTCTTGC TTAATGGGAT TTTGCTTTAA CTAAATATGT   2640
AAGTAAGGCC AAGGTAATGG AATGAAAAAT CTTCCTACTA AGGTATATGC TATTTGATAA   2700
AAAGACACTT TCTCCCTCCT CTCTCG                                       2726
```

SITE-SPECIFIC RECOMBINATION OF DNA IN PLANT CELLS

CROSS-REFERENCE TO RELATED APPLICATION

This application is a continuation-in-part of application Ser. No. 07/861,802, filed Feb. 19, 1991 (now abandoned), which was filed as a national stage application of PCT/US90/07295 (filed Dec. 19, 1990 and now abandoned), which is a continuation-in-part of application Ser. No. 07/455,221, filed Dec. 22, 19891 (now abandoned).

FIELD OF THE INVENTION

This invention relates to a method for producing site-specific recombination of DNA in plant cells and to the novel recombinant DNA constructs used to introduce and express the lox and cre components of the recombination system, as well as to transgenic lox and cre containing plants and their seeds.

BACKGROUND OF THE INVENTION

A variety of materials, systems and organisms have been the subject of genetic engineering to introduce systems to manipulate DNA.

Abremski et al., *Cell*, 32: 1301–1311 (1983) disclose a site-specific recombination system of bacteriophage P1. The system consists of a recombination site designated loxP and a recombinase designated Cre. Recombination between loxP sites on supercoiled, nicked-circle or linear DNA occurs in the presence of Cre.

Sauer, *Molecular and Cellular Biology*, 7: 2087–2096 (1987) discloses that the loxP-cre recombination system functions in the yeast *Saccharomyces cerevisiae*. This system was used to excise a gene located between two lox sites which had been introduced into the yeast genome. Cre was expressed from an inducible yeast GAL1 promoter and this cre gene was located on an autonomously replicating yeast vector.

Sauer and Henderson, *Proc. Natl. Acad. Sci. USA*, 85: 5166–5170 (1988) disclose that the loxP-cre recombination system functions in a transient manner in mouse cells in tissue culture. Cre was expressed from an inducible mouse metallothionein promoter, the cre gene being located on a papilloma virus replicon-containing vector. Excision of a gene located between two lox sites on a plasmid that was transiently introduced into cells, or of an insert in a gene of a herpesvirus vector, was demonstrated.

Sauer and Henderson, *Nucl. Acids Res.*, 17: 147–161 (1989) disclose that the loxP-cre recombination system functions in a stably transformed mouse tissue culture cell line. Cre, expressed from a rous sarcoma virus promoter, caused excision of a gene located between two lox sites that were integrated in the mouse cell genome.

Gatz and Quail, *Proc. Natl. Acad. Sci. USA*, 85: 1394–1397 (1988) disclose that expression of the bacterial tet repressor protein in plant protoplasts in culture in a transient manner results in regulation of a CaMV 35S promoter that has tet operator sequences added to it and is also transiently present in the protoplasts.

Baker et al., *Proc. Natl. Acad. Sci. USA*, 83: 4844–4848 (1986) disclose that the controlling element called "activator" that is derived from maize can excise itself after being introduced into the tobacco genome. Lassnet et al., *Mol. Gen. Genet.*, 218: 25–32 (1989) disclose that the "activator" element can be separated into two functional components: i) an element with a large internal deletion that cannot excise itself, but can be excised by ii) an element with a terminal deletion that cannot excise. These two components were separately transformed into tomato plants, brought together by genetic crosses, and shown to result in excision of the first component in some cells. This experiment indicates that elements from one plant genome can lead to recombination in heterologous plant cells, however the DNA sequences required for activity of the recombination site are not defined.

It is an object of the present invention to manipulate exogenous DNA once it is resident in the plant cell to enhance the ability to control trait expression in engineered plants. A feature of the present invention is the versatility of the method disclosed herein for producing site-specific recombination of DNA in plant cells in that the method is useful toward a wide variety of applications. These and other objects, features and advantages will become apparent upon having reference to the description of the invention herein.

SUMMARY OF THE INVENTION

The present invention provides a method for producing site-specific recombination of DNA in plant cells. The method (1) comprises:

i) introducing into the cells a first DNA sequence comprising a first lox site, and a second DNA sequence comprising a second lox site, and ii) contacting the lox sites with Cre, thereby producing the site-specific recombination.

In a preferred embodiment, a third DNA sequence comprising a cre gene is also introduced into the cells. This third DNA sequence may further comprise a promoter that is active in plant cells and expression of the cre gene is produced by direction of the promoter. Another method of the present invention is directed to method (1), wherein the first and second DNA sequences are introduced into two different DNA molecules and the site-specific recombination is a reciprocal exchange of DNA segments proximate to the lox sites.

The present invention also provides a method of excising exogenous genes or DNA segments in transgenic plants. This method comprises:

1) introducing into the cells a DNA sequence comprising a first lox site, a second lox site in the same orientation as the first lox site, and a gene or a DNA sequence there between; and 2) contacting the lox sites with Cre, thereby excising the heterologous gene or DNA sequence. The gene may be an undesired marker or trait gene.

Further claimed herein are plant cells transformed with a DNA sequence comprising at least one lox site, or with acre coding region. Various plants are also claimed herein, such as a plant containing cells transformed with acre coding region, preferably having argonomic or horticultural utility. Plasmids are claimed, having at least one lox site, a pre-selected DNA segment selected from the group consisting of a gene, a coding region and a DNA sequence that influences gene expression in plant cells. Similarly, DNA sequences are claimed, such as the sequence comprising at least one lox site and a pre-selected DNA segment selected from the group consisting of a gene, a coding region, and a DNA sequence that influences gene expression in plant cells.

Typical trait genes of interest in the present invention include those encoding enzymes or other proteins to confer altered oil composition in seed; altered seed protein composition; altered carbohydrate composition in seed; altered carbohydrate composition in fruit; altered pollen development properties; altered seed development; herbicide resistance; fungicide resistance; insecticide resistance; and the like.

Typical marker genes include those conferring hygromycin resistance, kanamycin resistance, bleomycin resistance, sulfonylurea resistance, streptomycin resistance or phosphinothricin resistance; or β-glucuronidase.

The gene may cause disruption of the cells expressing it such as ones encoding an RNase, restriction endonuclease, protease, a ribozyme, or an antisense RNA.

DNA segments of interest include those that reduce or block expression of an adjacent gene such as a polyadenylation nucleotide sequence or one with ATG sequence(s) in it.

The DNA segment may influence plant gene expression, including but not limited to a polyadenylation nucleotide sequence; a promoter; a regulatory nucleotide sequence; a coding region; a ribozyme; and an antisense RNA sequence. The DNA segment may provide expression of an inhibitor of a cell disruption gene.

Disclosed herein is an application of seed maternal tissue-specific and site directed DNA recombination for the production of seedless produce, in which seedlessness or less-seededness is a desirable trait, and plants are propagated by seeds or vegetatively. These crops include, but are not limited to, watermelon, melons, squash, cucumber, papaya, apple, pear, peach, tomato and grape.

BRIEF DESCRIPTION OF FIGURES

The invention will be more fully appreciated and understood upon having reference to the following Figures.

FIG. 6A is a photograph of the ethidium bromide-stained agarose gel from which total RNA samples were transferred to filters and analyzed by Northern blot analysis.

FIG. 6B presents the results of Northern blot analysis of total RNA samples obtained from various watermelon tissues.

FIG. 6C represents the results of Northern blot analysis wherein the filter from FIG. 6B, containing total RNA samples obtained from various watermelon tissues, was re-hybridized with freshly-made probe. X-ray film was overexposed in order to reveal any low level gene expression.

DETAILED DESCRIPTION OF THE INVENTION

Figure 1A:
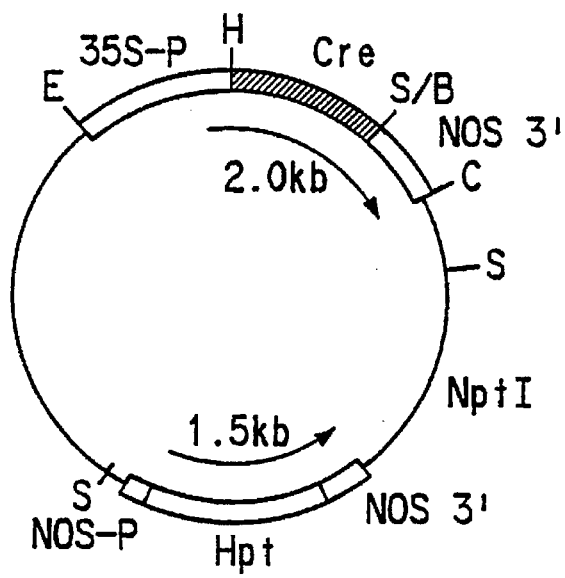
FIG. 1A shows the map of plasmid Cre/Hpt-A. Restriction sites used in making the construction are marked as B: BamHI, C: ClaI, E: EcoRI, H: HindIII, P: PstI, S: SalI and X: XbaI.

In the method of the invention using three DNA sequences, the first and second DNA sequences may be introduced into the cells connected by a pre-selected DNA segment. In such a case, the first and second lox sites may have the same orientation and the site-specific recombination of DNA is a deletion of the pre-selected DNA segment. The cre coding region may be derived from bacteriophage P1, and the first and second lox sites may be loxP or derivatives thereof. The pre-selected DNA segment is selected from the group consisting of a gene, a coding region, and a DNA sequence that influences gene expression in plant cells. Alternatively the segment may be an undesired marker or trait gene. The first and second lox sites may be selected to have opposite orientations and the site-specific recombination may be an inversion of the nucleotide sequence of the pre-selected DNA segment. In such case, the same selection of cre coding region, lox sites, and pre-selected DNA segment as referenced earlier are preferred. Similarly, in the aforementioned procedure wherein DNA sequences are introduced into two different DNA molecules, selections of cre coding region and lox sites as referenced earlier are also preferred. Plant cells of the invention may contain Cre protein or be transformed with a DNA sequence comprising at least one lox site. In the latter case, in such plants the DNA sequence may comprise two lox sites and a cre coding region, and preferably exhibit agronoic or horticultural utility. Plasmids, according to the invention, may have at least one lox site and a DNA sequence that influences gene expression in plant cells. For this type of plasmid, the DNA sequence may be a polyadenylation nucleotide sequence derived from the ribulose hisphosphate carboxylase (Rubisco) small subunit gene. Alternatively, the DNA sequence is a promoter, or a regulatory nucleotide sequence. In the plasmid the DNA sequence may be a selection marker. Of particular interest is a plasmid having a cre coding region and a promoter that is active in plant cells. Particular plasmids of interest include Plasmid Cre/Hpt-A (characterized by the restriction enzyme map shown in FIG. 1A, or a derivative thereof), Cre/Hpt-B (characterized by the restriction enzyme map shown in FIG. 1B, or a derivative thereof), loxP/NptII/Hra (characterized by the restriction enzyme map shown in FIG. 1C, or a derivative thereof) and pZ241oxAG (characterized by the restriction map shown in FIG. 4, or a derivative thereof). Of particular interest is the use of the methods of the invention in the manufacture of seedless produce.

As used herein, the expression "site-specific recombination" is intended to include the following three events:

1. deletion of a pre-selected DNA segment flanked by lox sites,
2. inversion of the nucleotide sequence of a pre-selected DNA segment flanked by lox sites, and 3. reciprocal exchange of DNA segments proximate to lox sites located on different DNA molecules.

It is to be understood that this reciprocal exchange of DNA segments can result in an integration event.

In the context of this disclosure, a number of terms shall be utilized.

The expression "nucleotide sequence" refers to a polymer of DNA or RNA, which can be single- or double-stranded, optionally containing synthetic, non-natural, or altered nucleotides capable of incorporation into DNA or RNA polymers.

"DNA segment" refers to a linear fragment of single- or double-stranded deoxyribonucleic acid (DNA), which can be derived from any source. The expression "DNA in plant cells" includes all DNA present in plant cells. As used herein, a "gene" is intended to mean a DNA segment which is normally regarded as a gene by those skilled in the art.

"Coding region" refers to a DNA segment which encodes a regulatory molecule or any polypeptide.

The expression "regulatory molecule" refers to a polymer of ribonucleic acid (RNA), such as antisense RNA or a ribozyme, or a polypeptide which is capable of enhancing or inhibiting expression of a gene product.

The term "expression" as used herein is intended to mean the synthesis of gene product from a gene coding for the sequence of the gene product. The gene product can be an RNA or a protein.

As used herein, the term "promoter region" refers to a sequence of DNA, usually upstream (5') of the coding sequence, which controls the expression of the coding region by providing the recognition for RNA polymerase and/or other factors required for transcription to start at the correct site. A "promoter fragment" constitutes a DNA sequence consisting of the promoter region.

A promoter region can include one or more regions which control the effectiveness of transcription initiation in response to physiological conditions, and a transcription initiation sequence.

"Tissue specific promoters" as referred to herein are those that direct gene expression primarily in specific tissues such as roots, leaves, stems, pistils, anthers, flower petals, seed coat, seed nucellus or epidermal layers. Transcription stimulators, enhancers or activators may be integrated into tissue specific promoters to create a promoter with a high level of activity that retains tissue specificity.

"Regulatory nucleotide sequence", as used herein, refers to a nucleotide sequence located proximate to a coding region whose transcription is controlled by the regulatory nucleotide sequence in conjunction with the gene expression apparatus of the cell. Generally, the regulatory nucleotide sequence is located 5' to the coding region. A promoter can include one or more regulatory nucleotide sequences.

"Polyadenylation nucleotide sequence" or "polyadenylation nucleotide region" refers to a nucleotide sequence usually located 3' to a coding region which controls the addition of polyadenylic acid to the RNA transcribed from the coding region in conjunction with the gene expression apparatus of the cell.

"DNA segment that influences gene expression in plant cells" can include a coding region, a promoter, a regulatory nucleotide sequence, a polyadenylation nucleotide sequence, or other DNA sequence regarded as influencing gene expression by those skilled in the art.

As used herein, "transformation" means processes by which cells/tissues/plants acquire properties encoded on a nucleic acid molecule that has been transferred to the cell/tissue/plant. "Transferring" refers to methods to transfer DNA into cells including, but not limited to, microinjection, permeabilizing the cell membrane with various physical (e.g., electroporation) or chemical (e.g., polyethylene glycol, PEG) treatments, high-velocity microprojectile bombardment also termed biolistics, or infection with *Agrobacterium tumefaciens* or *A. rhizogenes*. As used herein, "transformant" means a plant which has acquired properties encoded on a nucleic acid molecule that has been transferred to cells during the process known as transformation. As used herein, "re-transformation" means transformation of cells/tissues/plants which are in themselves transformants.

As used herein, "seed maternal tissue" refers to those seed tissues that are genetically identical to the mother plant. These are tissues outside of those resulting from the double fertilization (embryo and endosperm). At different stages of seed development, seed maternal tissues include integuments, seed coats, nucellus and integumentary tapetum.

As used herein "seedless" refers to fruits that are entirely seedless or much reduced in seed number per fruit. Examples of the former are banana and pineapple; whereas an example of the latter is actually the "seedless" watermelon which always contains many immature white seeds and a few fully developed seeds.

As used herein, "sexual hybridization" means the production of offspring by crossbreeding of two plants that are genetically different, such as those which have different DNA sequences integrated into their genome.

As used within "integrated" means that the transferred DNA is incorporated into the plant genome.

As used herein the expression "lox site" means a nucleotide sequence at which the gene product of the cre gene, referred to herein as Cre, can catalyze a site-specific recombination. The loxP site is a 34 base pair nucleotide sequence which can be isolated from bacteriophage P1 by methods known in the art. One method for isolating a loxP site from bacteriophage P1 is disclosed by Hoess et al., *Proc. Natl. Acad. Sci. USA*, 79: 3398 (1982). The loxP site consists of two 13 base pair inverted repeats separated by an 8 base pair spacer region. The nucleotide sequences of the inverted repeats and the spacer region are as follows:

ATAACTTCGTATA ATGTATGC TATACGAAGTTAT.

*E. coli* transformed with plasmid loxP/NptII/Hra carrying two lox sites, one on either side of a polyadenylation nucleotide sequence derived from a tobacco Rubisco small subunit gene, has been deposited with the ATCC under the Budapest treaty agreement and bears deposit accession number 68177. This and other deposits are available to the public upon the grant of a patent to the assignee. However, it should be understood that the availability of a deposit does not constitute a license to practice the subject invention in derogation of patent rights granted by governmental action. The lox sites and intervening region can be excised from plasmid loxP/NptII/Hra with the restriction enzyme HindIII. In addition, a preselected DNA segment can be inserted into loxP/NptII/Hra at the BamHI restriction enzyme site by techniques known in the art. Other suitable lox sites include loxB, loxL and loxR sites which are nucleotide sequences isolated from *E. coli*. These sequences are disclosed and described by Hoess et al., *Proc. Natl. Acad. Sci. USA*, 79: 3398 (1982). Lox sites can also be produced by a variety of synthetic techniques which are known in the art. For example, synthetic techniques for producing lox sites are disclosed by Ito et al., *Nuc. Acid Res.*, 10: 1755 (1982) and Ogilvie et al., *Science*, 214: 270 (1981).

Methods for introducing a DNA sequence into plant cells are known in the art. Nucleic acids can generally be introduced into plant protoplasts, with or without the aid of electroporation, polyethylene glycol, or other processes known to alter membrane permeability. Nucleic acid constructs can also be introduced into plants using vectors comprising part of the Ti- or Ri-plasmid, a plant virus, or an autonomously replicating sequence. Nucleic acid constructs can also be introduced into plants by microinjection or by high-velocity microprojectiles, also termed "particle bombardment" or "biolistics" [Sanford, J. C., Tibtech 6: 299 (1988)], directly into various plant parts. The preferred means of introducing a nucleic acid fragment into plant cells involves the use of A. tumefaciens containing the nucleic acid fragment between T-DNA borders either on a disarmed Ti-plasmid (that is, a Ti-plasmid from which the genes for tumorigenicity have been deleted) or in a binary vector in trans to a disarmed Ti-plasmid. The Agrobacterium can be used to transform plants by inoculation of tissue explants, such as stems, roots, or leaf discs, by co-cultivation with plant protoplasts, or by inoculation of seeds or wounded plant parts.

The range of crop species in which foreign genes can be introduced is increasing rapidly as tissue culture and transformation methods improve and as selectable markers become available. Thus, this invention is applicable to a broad range of agronomically or horticulturally useful plants. The particular method which is employed to introduce the DNA sequence into a selected plant cell is not critical. In a preferred embodiment, DNA sequences are introduced into plant cells by co-cultivation of leaf discs with A. tumefaciens essentially as described by Horsch et al., Science, 227: 1229–1231 (1985) omitting the nurse cultures.

In the present method, the lox sites are contacted with Cre, thereby producing the site specific recombination. In one embodiment, Cre or cre messenger RNA is introduced into the cells directly by micro-injection, biolistics, or other protein or RNA introduction procedure. In a preferred embodiment, the cre coding region is introduced into the plant cell under the control of a promoter that is active in plant cells. Suitable regulatory nucleotide sequences are known in the art. The promoter which is employed with a selected plant cell is not critical to the method of the invention. A partial list of suitable promoters include the 35S promoter of cauliflower mosaic virus described by Odell et al., Nature, 313: 810–812 (1985); the promoter from the nopaline synthase gene of A. tumefaciens described by Depicker et al., J. of Mol, Appl. Genet., 1: 561–573 (1982); the promoter from a Rubisco small subunit gene described by Mazur and Chui, Nucleic Acids Research 13: 2373–2386 (1985); the 1' or 2' promoter from the TR-DNA of A. tumefaciens described by Velten et al., EMBO J. 12: 2723–2730 (1984); the promoter of a chlorophyll a/b binding protein gene described by Dunsmuir et al., J. Mol. Appl. Genet. 2: 285–300 (1983); the promoter of a soybean seed storage protein gene described by Chen et al., Proc. Natl. Acad. Sci. USA, 83: 8560–8564 (1986); and the promoter from the wheat EM gene described by Marcotte et al., Nature 335: 454–457 (1988). Cre can be expressed throughout the plant generally in all cells at all stages of development, or expression of cre can be more specifically controlled through the use of promoters or regulatory nucleotide sequences having limited expression characteristics. Cre can be expressed in a tissue specific manner, for example only in roots, leaves, or certain flower parts. Cre can be expressed in a developmentally specific time period, for example only during seed formation or during reproductive cell formation. Cre expression can also be placed under the control of a promoter that can be regulated by application of an inducer. In this case cre expression is off or very low until the external inducer is applied. Promoters active in plant cells have been described that are inducible by heat shock [Gurley et al., Mol. Cell. Biol. 6: 559–565 (1986)], ethylene [Bfoglie et al., Plant Cell 1: 599–607 (1989)], auxin [Hagan and Guilfoyle, Mol. Cell. Biol. 5: 1197–1203 (1985)], abscisic acid [Marcotte et al., Nature 335: 454–457 (1988)], salicylic acid (EPO 332104A2 and EPO 337532A1), and substituted benzenesulfonamide safeners (WO 90/11361). Control of cre expression by the safener-inducible promoter 2-2, or its derivatives, allows the expression to be turned on only when the inducing chemical is applied and not in response to environmental or phytohormonal stimuli. Thus cre expression can be initiated at any desired time in the plant life cycle. Preferably, the regulatory nucleotide sequence is a 35S promoter or a 2-2 promoter.

The gene product of the cre coding region is a recombinase herein designated "Cre" which effects site-specific recombination of DNA at lox sites. As used herein, the expression "cre coding region" means a nucleotide sequence which codes for a gene product which effects site-specific recombination of DNA in plant cells at lox sites. One cre coding region can be isolated from bacteriophage P1 by methods known in the art. One method for isolating a cre coding region from bacteriophage P1 is disclosed by Abremski et al., Cell, 32: 1301–1311 (1983). The naturally occurring cre coding region can be altered by mutation to produce Cre proteins with altered properties as described by Wierzbicki et al., J. Mol. Biol., 195: 785–794 (1987). These altered Cre proteins retain their identities as Cre.

E. coli transformed with plasmid Cre/Hpt-A and E. coli transformed with plasmid Cre/Hpt-B both carrying a cre coding region isolated from bacteriophage P1 and a cauliflower mosaic virus (CaMV) 35S promoter have been deposited with the ATCC (American type Culture Collection, 12301 Parklawn Drive, Rockville, Md. 20852) on 16 Nov. 1989 and bear deposit accession numbers ATCC 68176 and ATCC 68175, respectively. The cre coding region can be isolated from plasmid Cre/Hpt-B with the restriction enzymes KpnI and SalI.

In one embodiment, the first, second, and optionally, third DNA sequences are introduced into one plant by transformation either in one step or in two or three successive steps. Alternatively, the first and second DNA sequences are introduced into one plant and the third DNA sequence into a different plant. The two plants are then sexually hybridized to produce progeny having all three DNA sequences. In another embodiment the first, second, and third DNA sequences are each introduced separately into a plant and the three are brought together by sexual hybridization.

Most preferably, the plasmid for introducing a DNA sequence comprising a promoter and a cre coding region is Cre/Hpt-A or Cre/Hpt-B and the plasmid for introducing a DNA sequence comprising a lox site is loxP/NptII/Hra or derivatives thereof carrying a pre-selected DNA segment other than or in addition to the Rubisco small subunit polyadenylation nucleotide sequence located between the first and second lox sites. These plasmids can be used to generate plants carrying cre or lox by those skilled in the art or as taught in this application. A Cre plant and a lox plant can be sexually hybridized to produce hybrid progeny plants containing a cre coding region and lox sites.

Since the lox site is an asymmetrical nucleotide sequence, the lox sites on the same DNA molecule can have the same or opposite orientation with respect to each other. Recombination between lox sites in the same orientation results in a deletion of the DNA Segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the product of the cre coding region.

In a preferred embodiment of the present invention, the first and second DNA sequences are introduced into plant cells connected by a pre-selected DNA segment. The segment can be a gene or any other sequence of deoxyribonucleotides of homologous, heterologous or synthetic origin. Preferably, the pre-selected DNA segment is a gene for a structural protein, an enzyme, or a regulatory molecule; or a DNA sequence that influences gene expression in plant cells such as a regulatory nucleotide sequence, a promoter, or a polyadenylation nucleotide sequence. If the first and second lox sites have the same orientation, contact with Cre produces a deletion of the pre-selected DNA segment. If the first and second lox sites have opposite orientation, contact with Cre produces an inversion ("flipping") of the nucleotide sequence of the pre-selected DNA segment.

An effort was made to demonstrate the activation of gene expression using the flipping mode of the loxP-cre system. A construction was made in which the coding and polyadenylation regions from a sulfonylurea-resistant ALS gene were placed between two synthetic loxP sites that were in inverted orientation relative to each other. This loxP bounded fragment was placed in inverted orientation to the 35S promoter such that it would not be expressed. The entire interrupted gene was put into a binary vector including a kanamycin resistance selection marker, introduced into A. tumefaciens, and then into tobacco plants. As expected, kanamycin-resistant transformants were not resistant to chlorsulfuron (a sulfonylurea), demonstrating no expression of the inverted coding region. Tissue was taken from selected transformants and retransformed using Agrobacterium containing –/Hpt or Cre/Hpt-B (Example 4). Hygromycin selected plants that received Cre retained their sensitivity to chlorsulfuron, indicating that the sulfonylurea-resistant ALS gene was not activated. The ALS gene was not activated because the loxP-bounded fragment did not flip in the plants. This was determined by analyzing plant DNA on Southern blots: a band representing the original lox construction was detected, but no band representing the flipped loxP-bounded fragment was detected. The loxP-bounded fragment was then shown to be incapable of flipping in an in vitro reaction using purified Cre. Thus this particular lox construction was defective in some as yet undetermined aspect. It is fully anticipated that if the loxP-bounded fragment were capable of flipping in the in vitro reaction, it would flip in plants containing Cre and the ALS gene would be activated.

UTILITY

The invention permits the site-specific recombination of DNA at the points of the introduced lox sites in any of the following ways:
(a) Deletion of the DNA segment flanked by lox sites (excision);
(b) Inversion of the nucleotide sequence of the DNA segment flanked by lox sites (flipping); or
(c) reciprocal exchange of DNA segments proximate to lox sites located on different molecules (exchange).

Mode (a), excision, occurs when the lox sites are in like orientation on the same DNA molecule. One example of this event is to permit the removal of undesired marker genes, such as those that confer antibiotic resistance or herbicide resistance, in transgenic plants. Removal of the marker would also allow the use of the same marker in a second transformation of the transgenic plant. Also a trait gene that is undesired in a specific tissue or at a certain developmental time can be excised. Also a DNA sequence influencing expression of a gene can be excised resulting in increased or decreased expression of the gene. One skilled in the art will recognize that the reverse of excision (i.e., integration) may also be performed.

Mode (b), flipping, occurs when the lox sites are in reverse orientation on the same DNA molecule. This event may provide new methods of cre-regulated gene expression. Gene expression can be turned on by changing the direction of a promoter or regulatory nucleotide sequence from an inactive to an active orientation with respect to a coding region. Also changing the orientation of a coding region with respect to a promoter will alter its expression. Other ways to turn expression of a gene off include flipping an antisense RNA or ribozyme from an inactive to an active orientation.

Mode (c), exchange, may provide useful tools for recombinant alterations of plant DNA.

One application of the instant invention is in controlling male fertility in a method for producing hybrid crops. Hybridization of a crop involves the crossing of two different lines to produce hybrid seed from which the crop plants are grown. Hybrid crops are superior in that more of the desired traits can be introduced into the production plants. For instance, quality traits such as oil content, herbicide resistance, disease resistance, adaptability to environmental conditions, and the like, can be hybridized in offspring so that the latter are invested with the most desirable traits of its parents. In addition, progeny from a hybrid cross may possess new qualities resulting from the combination of the two parental types, such as yield enhancement resulting from the phenomenon known as heterosis. Controlled cross-fertilization to produce hybrid seeds has been difficult to achieve commercially due to competing self-fertilization, which occurs in most crop plants.

Currently, hybrid seed production is performed by one of the following means: (a) mechanically removing or covering the male organs to prevent self-fertilization followed by exposing the male-disabled plants to plants with male organs that contain the trait(s) desired for crossing; (b) growing genetically male-sterile plants in the presence of plants with fertile male organs that contain the trait that is desired for crossing; or (c) treating plants with chemical hybridizing agents (CHA) that selectively sterilize male organs followed by exposing the male-disabled plants to plants with fertile male organs that contain the trait that is desired for crossing. Some disadvantages to each of these methods include: (a) applicability only to a few crops, such as corn, where the male and female organs are well separated; and it is labor intensive and costly; (b) genetically male sterile lines are cumbersome to maintain, requiring crosses with restorer lines; (c) all CHAs exhibit some degree of general phytotoxicity and female fertility reduction. Also CHAs often show different degrees of effectiveness toward different crop species, or even toward different varieties within the same species.

A new molecular genetic approach to hybrid crop production that is applicable to a wide range of crops and involves genetic male sterility has been developed by Plant Genetic Systems. As described in EPA 89-344029, this system involves the introduction of a cell disruption gene that is expressed only in the tapetal tissue of anthers thereby destroying the developing pollen. The resulting genetically male sterile plants serve as the female parents in the cross to produce hybrid seed. This system could be highly effective and desirable. However one disadvantage is that since the male sterile parent is heterozygous for the sterility gene which acts as a dominant trait, only 50% of the plants grown from the hybrid seed are fertile, the rest retain the sterility gene. This situation will result in reduced pollen shed in the production field which may lead to reduced seed set and yield. Addition of loxP-cre technology to this hybrid scheme will allow restoration of fertility to a much higher percentage of plants in the production field, as well as elimination of the cell disruption gene. Placing the male sterility gene between loxP sites allows it to be deleted following introduction of Cre into the hybrid from the male parent.

Another application of the instant invention is in making seedless produce. Seedlessness is desirable in consumed produce for convenience and taste. Currently "seedless" watermelon is sold that actually contains some developed seed and a large number of immature seed that varies in size up to that of fully mature seed. To produce these watermelon first a hybrid cross is made between a tetraploid maternal parent and a diploid pollinator. The resulting triploid seed produces self-infertile plants that are crossed with a diploid pollinator to produce seedless fruit [H. Kihara, *Proc. Soc. Hort. Sci.*, 58: 217–230, (1951)]. This production scheme suffers the following problems: (i) Creating a tetraploid plant, which is accomplished by a chromosome duplication method, is difficult. Also the number of seeds per fruit on this tetraploid plant must be low since this has a positive correlation with seed number in the final product [C. F. Andrus, *Production of Seedless Watermelons*, USDA Tech. Bull. No. 1425 (1971)]. (ii) Good combining ability of the diploid pollinator and the tetraploid plant is difficult to achieve [W. R. Henderson, *J. Amer. Soc, Hort. Sci.*, 102: 293–297 (1977)]. (iii) The triploid seeds are much inferior to regular diploid seeds in vigor and germinability [D. N. Maynard, *Hort. Sci.*, 24: 603–604 (1989)]. These problems, together with incomplete seedlessness in the final product, make the development of seedless watermelon slow and difficult. This ploidy-based approach to seedlessness is possible only in those few species where unusual euploidy plants (tetraploid and triploid for watermelon, for example) are viable.

A molecular genetic approach to seedlessness involving loxP-cre is much more efficient, resulting in a more reliably seedless product and does not involve changes in ploidy. Thus it is more generally applicable to a wider range of species. A lox/polyA-inactivated cell disruption gene regulated by a seed-specific promoter is introduced into a plant. When this plant is crossed to a plant expressing Cre, the disruption gene is activated and expressed in the seed, thereby disrupting seed development. The certainty of endosperm failure (caused by the cell disruption gene product) leading to the abortion of the whole seed is very high. In most dicots, the endosperm supplies the nutrients needed for early embryo development. Endosperm abortion invariably leads to seed abortion [R. A. Brink and D. C. Cooper, *Bot. Rev.* 8: 423–541 (1947)].

The seed-specific promoter used is selected from the group of promoters known to direct expression in the embryo and/or the endosperm of the developing seed, most desirably in the endosperm. Examples of seed-specific promoters include but are not limited to the promoters of seed storage proteins. The seed storage proteins are strictly regulated, being expressed almost exclusively in seeds in a highly tissue-specific and stage-specific manner [Higgins et al., *Ann. Rev. Plant Physiol.* 35: 191–221 (1984); Goldberg et al., *Cell* 56: 149–160 (1989)]. Also, different seed storage proteins may be expressed at different stages of seed development and in different parts of the seed.

There are numerous examples of seed-specific expression of seed storage protein genes in transgenic dicotyledonous plants. These include genes from dicotyledonous plants for bean β-phaseolin [Sengupta-Goplalan et al., *Proc. Natl. Acad. Sci. USA* 82: 3320–3324 (1985) and Hoffman et al., *Plant Mol. Biol.* 11: 717–729 (1988)], bean lectin [Voelker et al., *EMBO J* 6: 3571–3577 (1987(], soybean lectin [Ocamuro et al., *Proc. Natl. Acad. Sci. USA* 83: 8240–8344 (1986)]. soybean kunltz trypsin inhibitor [Perez-Grau and Goldberg *Plant Cell* 1: 1095–1109 (1989)], soybean β-conglycinin [Beachy et al., *EMBO J* 4: 3047–3053 (1985), Barker et al., *Proc. Natl. Acad. Sci.* 85: 458–462 (1988), Chen et al., *EMBO J* 7: 297–302 (1988), Chen et al., *Dev. Genet,* 10: 112–122 (1989), Naito et al., *Plant Mol. Biol.* 11: 683–695 (1988)], pea vicillin [Higgins et al., *Plant Mol. Biol.* 11: 109–123 (1988)], pea convicilllin (Newbigin et al., *Planta* 180: 461 (1990)], pea legumin [Shirsat et al., *Mol. Gen. Genetics* 215: 326 (1989)], rapeseed napin [Radke et al., *Theor. Appl. Genet.* 75: 685–694 (1988)], as well as genes from monocotyledonous plants such as for maize 15-kd zein [Hoffman et al., *EMBO J* 6: 3213–3221 (1987)], barley β-hordein [Marris et al., *Plant Mol. Biol.* 10: 359–366 (1988)], and wheat glutenin [Colot et al., *EMBO J* 6: 3559–3564 (1987)]. Moreover, promoters of seed-specific genes operably linked to heterologous coding regions in chimeric gene constructions also maintain their temporal and spatial expression pattern in transgenic plants. Such examples include *Arabidopsis thaliana* 2S seed storage protein gene promoter to express enkephalin peptides in Arabidopsis and *Brassica napus* seeds [Vandekerckhove et al., *Bio/Technology* 7: 929–932 (1989)], bean lectin and bean β-phaseolin promoters to express luciferase [Riggs et al., *Plant Sci.* 63: 47–57 (1989)], and wheat glutenin promoters to express chloramphenicol acetyl transferase [Colot et al., *EMBO J.* 6: 3559–3564 (1987)]. Promoters highly expressed early in endosperm development are most effective in this application. Of particular interest is the promoter from the a subunit of the soybean β-conglycinin gene [Walling et al., *Proc. Natl. Acad, Sci. USA* 83: 2123–2127 (1986)] which is expressed early in seed development in the endosperm and the embryo.

The cell disruption gene used is selected from a group of genes encoding products that disrupt normal functioning of cells. There are many proteins that are toxic to cells when expressed in an unnatural situation. Examples include the genes for the restriction enzyme EcoRI [Barnes and Rine, *Proc. Natl. Acad. Sci. USA* 82: 1354–1358 (1985)], diphtheria toxin A [Yamaizumi et al., *Cell* 15: 245–250 (1987)], streptavidin [Sano and Cantor, *Proc. Natl. Acad. Sci. USA* 87: 142–146 (1990)], and barnase [Paddon and Hartley, *Gene* 53: 11–19 (1987)]. Most preferred for this system is the coding region of barnase which has been shown to be highly effective in disrupting the function of plant cells (EPA 89-344029).

A highly desirable seedless system is one in which fully fertile F1 seed develops, that can then be grown into plants that produce only seedless fruit. This system is economically favorable in that for each cross pollination, a large number of seedless fruits result: the number of F1 seed from one cross X the number of fruits produced on an F1 plant. Also incorporated in this scheme are the advantages of growing a hybrid crop, including the combining of more valuable traits and hybrid vigor. This is accomplished in the same manner as described above except that the lox/polyA-inactivated disruption gene is expressed from a seed maternal tissue (seed coat or nucellus)-specific promoter. For example, the seed coat is the outgrowth of the integuments, a strictly maternal tissue. Therefore the hybrid cross that brings the lox/polyA-inactivated disruption gene together with the cre gene does not involve this seed coat tissue. The seed coat of the F1 seed has either lox or cre, depending on which is used as the female parent, and thus F1 seed develop normally. After the F1 seed gives rise to a fruit-bearing F1 plant, all vegetative cells (including seed coat cells) inherit both lox and cre from the embryo. Thus the seed coat of the F1 plant has an activated cell disruption gene.

The seed coat is an essential tissue for seed development and viability. When the seed is fully matured, the seed coat serves as a protective layer to inner parts of the seed. During seed development, the seed coat is a vital nutrient-importing tissue for the developing embryo. The seed is nutritionally "parasitic" to the mother plant. All raw materials necessary for seed growth must be imported. In seeds of dicotyledonous plants, the vascular tissue enters the seed through the funiculus and then anastamoses in the seed coat tissue. There is no vascular tissue connection or plasmodesmata linkage between the seed coat and the embryo. Therefore, all nutrient solutes delivered into the developing seed must be unloaded inside the seed coat and then move by diffusion to the embryo. Techniques have been developed to study the nutrient composition in the seed coat [Hsu et al., *Plant Physiol.* 75: 181 (1984); Thorne & Rainbird, *Plant Physiol.* 72: 268 (1983); Patrick, *J. Plant Physiol.* 115: 297 (1984); Wolswinkel & Ammerlaan, *J. Exp. Bot.* 36: 359 (1985)], and also the detailed cellular mechanisms of solute unloading [Offler & Patrick, *Aust. J. Plant Physiol.* 11: 79 (1984); Patrick, *Physiol. Plant* 78: 298 (1990)]. It is obvious that the destruction of this vital nutrient-funnelling tissue causes seed abortion.

Seedless Fruit Production

Seedless fruit production is a novel application of tissue-specific and site-directed DNA recombination. This method is useful for the production of seedless watermelon. A combination of gene expression specific for maternally inherited seed tissue and the lox-Cre system is used for the production of seedless watermelon. The system can be universally applied to any horticultural crop in which the presence of seeds is undesirable and difficult to be eliminated through conventional breeding methods. The system also allows the normal production of F1 seeds. The ability to maintain heterosis is an advantage of producing F2 seedless fruits.

The existing production of seedless watermelon indicates that seed development is not essential for the watermelon fruit development. However, conventional production of seedless watermelon using the ploidy imbalance trick has never been very popular due to the difficulty of overcoming the yield and production problems. Creating and maintaining the tetraploid (4n) female germline, and producing the triploid (3n) seeds have made the seed cost high. Cross-pollination is needed for the production of triploid seeds (4n×2n) and seedless fruits (3n×2n). Also triploid seed germination is usually poor due to ploidy imbalance.

The present approach eliminates the dependence on polyploid germlines and provides an efficient system for producing seedless fruit. In addition to the site-directed DNA recombination, the uniqueness of this invention lies in the understanding of seed development and utilization of seed-specific yet maternally-inherited gene expression. The products of double fertilization of higher plants are the embryo and endosperm. The seed coat (including the integumentary tapetum) and nucellus (the tissue encompassing the embryo sac) are the remaining seed tissues that are maternally inherited. In addition to general protection, the seed coat and nucellus also play an important role in importing nutrients into the developing embryo and endosperm. Seed development will be aborted if this vital nutrient-importing mechanism of the seed coat/nucellus is debilitated. This will be accomplished by using the lox-Cre system to activate a cell-damaging gene only in these tissues. Controlling the gene activation in a maternal tissue-specific manner allows production of normal F1 seed, but abortion of F2 seed. A seed coat or nucellus promoter is coupled to a tissue-destructive (lethal) gene in order to prevent seeds from forming. The destructive gene is inactive in the seed parent due to the presence of a blocking transcription terminator. The terminator is flanked by lox sites for subsequent excision by a Cre-mediated recombination event. The Cre protein is also controlled by the seed coat/nucellus-specific promoter. When plants carrying the separate Cre and lox constructs are crossed, the F1 seed will be viable because seed coat/nucellus is maternal tissue, and in that tissue Cre and lox elements are not combined. When the F1 seed is used as planting seed, the self-pollinated or out-crossed plants will produce seedless fruits or vegetables, since in seed coat/nucellus tissues Cre and lox elements are combined, and the lethal gene is activated. Examples 13–15, below describe the isolation of a nucellus-specific gene.

Seedless fruit production may be accomplished by other methods making use of the watermelon nucellus-specific gene of SEQ ID No. 1, or other seed maternal tissue-specific gene. Disruption of seed development through inhibiting expression of an important maternal seed tissue-specific gene leads to seedless fruit production. Expression of a maternal seed tissue gene may be inhibited by expression of antisense RNA for that gene's coding region; also by cosuppression brought about by integration of a copy or copies of the sense gene that are in addition to the endogenous copy or copies. In this scheme vegetative propagation of the plant is required, since the plant is always seedless. In another method, the promoter from the watermelon nucellus-specific gene of SEQ ID No.1, or the promoter from another seed maternal tissue-specific gene is used to express a gene product that is lethal to cells, thereby preventing seed development. In this scheme vegetative propagation of the plant is required, since the plant is always seedless.

The watermelon nucellus-specific promoter can be used as an embryo and pollen-specific promoter in transgenic Brassies, and soybean. It has been demonstrated that this promoter can function as an embryo and pollen-specific promoter in transgenic tobacco. Brassica, and soybean, like tobacco, do not contain a nucellus layer in their mature seeds.

This promoter may also be used to drive gene expression in embryo and pollen in these two species. It is of particular interest for use in expressing the genes encoding the enzymes involved in the lipid biosynthetic pathway to alter the fatty acid composition in these oil crops.

EXAMPLES

Site Specific Recombination in Plants

Materials and Methods

Molecular Techniques

Methods of culturing bacteria, preparing DNA, and manipulating DNA were as described by Maniatis et al., *Molecular Cloning: A Laboratory Manual* [Cold Spring Harbor Laboratory, New York (1982)] unless stated otherwise. Restriction enzymes and other enzymes used in DNA manipulations were obtained from New England Biolabs, Inc. (Beverly, Mass., USA), Boehringer Mannheim (Indianapolis, Ind., USA), or Bethesda Research Laboratory (Gaithersburg, Md., USA) and were used essentially according to the manufacturer's specifications.

Isolation and analysis of plant RNA and DNA

Both RNA and DNA were extracted from the same leaf samples by combining methods for extraction of each. One to five grams of leaf tissue were frozen in liquid nitrogen and ground. Frozen tissue was added to 15 ml of extraction buffer [100 mM Trizma hydrochloride (Tris) pH 8.0, 50 mM EDTA pH 8.0, 100 mM NaCl, 1% sodium dodecyl sulfate (SDS), 200 µg/ml proteinase K] and heated at 65° C. for 10 min. Five ml of 5M potassium acetate was added, and the samples were placed on ice for 20 min. The samples were spun at 25K×g for 20 min and the supernatant was poured through cheesecloth into a tube containing 1 ml of 5M sodium acetate and 10 ml of isopropanol. The tubes were left overnight at -20° C. The RNA/DNA was pelleted by centrifugation at 20K×g for 15 min. The pellets were resuspended in 10 mls of water and an equal volume of 4M lithium chloride was added. The solutions were placed on ice for 1–2 hours, then centrifuged for 20 min at 20K×g. The supernatant was collected and an equal volume of isopropanol was added. After an overnight incubation at -20° C., the DNA was pelleted and resuspended in a solution of 10 mM Tris with 1 mM EDTA pH 8.0 (TE). The samples were extracted with an equal volume of Tris pH 8.0 buffered phenol and precipitated by adding 0.1 volume of 3M sodium acetate and 2.5 volumes of ethanol. For Southern blot analysis the DNA was digested with a restriction enzyme and the resulting fragments were separated by gel electrophoresis, transferred to Zeta-Probe filters (Bio-Rad Laboratories, Richmond, Calif., USA), and hybridized with nick translated probes.

The lithium chloride pellet was resuspended in one-half the original volume of water, an equal volume of lithium chloride was added, and the mixture was placed on ice for an additional hour. The RNA was pelleted by centrifugation, resuspended in water, extracted with buffered phenol, and precipitated with 0.1 volume of 3M sodium acetate and two volumes ethanol. For Northern blot analysis the RNA was separated by gel electro-phoresis in formaldehyde as described by Rave et al., Nucl. Acids Res. 6: 3559–3569 (1979), transferred to Zeta-Probe filters, and hybridized to nick translated probes.

Generation of transgenic plants The cointegrate and binary Ti plasmids containing the chimeric cre gene and those containing loxP sites were introduced into tobacco by leaf disk transformation and into Arabidopsis by root transformation as described in Example 8. Standard aseptic techniques for the manipulation of sterile media and axenic plant/bacterial cultures were followed, including the use of a laminar flow hood for all transfers. Recipes for media for tobacco are given in Table 2. Potted tobacco plants for leaf disk infections were grown in a growth chamber maintained for a 14 hr, 24° C. day, 10 hr, 20° C. night cycle, with approximately 80% relative humidity, under mixed cool white fluorescent and incandescent lights. Tobacco leaf disk infections were carried out essentially by the method of Horsch et al., Science 227, 1229–1231 (1985), omitting nurse cultures.

Healthy young leaves, not fully expanded and approximately 3–5 inches in length, were harvested from approximately 4–6 week old tobacco plants (Nicotiana tabacum var. Xanthi). The leaves were surface sterilized by immersion in a solution containing 10% commercial bleach and 0.1% sodium dodecyl sulfate (SDS). After 20 minutes of sterilization with intermittent mixing, the leaves were transferred successively three times to sterile deionized water to rinse the leaves thoroughly, and then shaken gently to remove excess water. Leaf disks, 8 mm in diameter, were prepared from whole leaves using a sterile paper punch.

Cultures of Agrobacterium cells containing the binary or cointegrate plasmids were grown in 5 ml of YEB or YEP broth (Table 1 and Table 8) with the appropriate antibiotics. Cultures were grown for approximately 17–20 hours in 18 mm glass culture tubes in a New Brunswick platform shaker maintained at 28° C. Leaf disks were inoculated by submerging them for several minutes in 20 ml of a 1:20 dilution of the overnight Agrobacterium culture.

After inoculation, the leaf disks were placed in petri dishes containing 0.1N1B agar medium (Table 2). The dishes were sealed with parafilm and incubated under mixed fluorescent and "Gro and Sho" plant lights (General Electric) for 2–3 days in a culture room maintained at approximately 25° C.

To rid the leaf disks of Agrobacterium and to select for the growth of transformed tobacco cells, the leaf disks were transferred to fresh 0.1N1B medium containing 500 mg/l cefotaxime and either 10–30 mg/l hygromycin, most preferably 30 mg/l hygromycin, 20–50 ppb chlorsulfuron, most preferably 25 ppb chlorsulfuron, or 100–300 mg/l kanamycin, most preferably 100 mg/l kanamycin. Cefotaxime was kept as a frozen 200 mg/ml stock solution and added aseptically (filter sterilized through a 0.45 µm filter) to the media after autoclaving. A fresh stock of hygromycin, chlorsulfuron, or kanamycin was made for each use and was filter sterilized into the autoclaved media.

Leaf disks were incubated under the growth condition described above for 2–3 weeks and then transferred to fresh media of the same composition or to MX⁻ with the appropriate antibiotics.

Approximately 3–4 weeks later, shoots developing on medium containing either hygromycin, chlorsulfuron, or kanamycin were excised with a sterile scalpel and planted in MX⁻ medium (Table 2) containing 200–500 mg/l cefotaxime, most preferably 250 mg/l cefotaxime, in the presence or absence of 10–30 mg/l hygromycin, most preferably 30 mg/l hygromycin, or 20–30 ppb chlorsulfuron, most preferably 25 ppb chlorsulfuron. Root formation was recorded within 3 weeks.

Leaves were removed from the rooted excised shoots to determine levels of resistance to hygromycin, chlorsulfuron, or kanamycin in a callus induction assay on selective media. To induce callus formation, leaves were excised and leaf disks, 8 mm in diameter, were made using a sterile paper punch and plated on callus induction medium (Table 2) containing either 20–50 mg/l hygromycin, most preferably 30 mg/l hygromycin, 5–25 ppb chlorsulfuron, most preferably 25 ppb chlorsulfuron, or 50–100 mg/l kanamycin, most preferably 100 mg/l kanamycin. Callus growth on selective and non-selective media was recorded within 3 weeks.

TABLE 1

AGROBACTERIUM GROWTH MEDIA

| | Per Liter |
|---|---|
| YEB MEDIUM | |
| Bacto Beef Extract | 5.0 g |
| Bacto Yeast Extract | 1.0 g |
| Peptone | 5.0 g |
| Sucrose | 5.0 g |
| MgSO$_4$.7H$_2$O | 0.5 g |
| Agar (optional) | 15.0 g |
| pH 7.2 | |
| MIN A with sucrose plates | |
| water | 948 ml |
| agar | 15 g |
| mix and autoclave | 40 ml |
| min A salts: | |
| 200 ml: K$_2$HPO$_4$ | 52.5 g |
| KH$_2$PO$_4$ | 22.5 g |
| (NH$_4$)$_2$SO$_4$ | 5 g |
| Na Citrate 2H$_2$O | 2.5 g |
| 20% MgSO$_4$7H$_2$O | 1 ml |
| 1% thiamine hydrochloride | 0.5 ml |
| 20% sucrose | 10 ml |

TABLE 2

TOBACCO TISSUE CULTURE MEDIA

| | Per Liter |
|---|---|
| Callus Induction Medium | |
| Murashige's Minimal Organics Medium GIBCO #510-1118 (contains 3% sucrose) | 1 package |
| 100X Vitamin Supplement: 10 mg/l thiamine 50 mg/l pyridoxine 50 mg/l nicotinic acid | 10 ml |
| 1 mg/ml napthaleneacetic acid (NAA) stock | 1 ml |
| 1 mg/ml 6-Benzylaminopurine (BAP) stock | 0.2 ml |
| agar | 8.0 g |
| pH 5.8 | |
| Shoot Induction Medium (.1N1B) | |
| Murashige's Minimal Organics Medium GIBCO #510-1118 (contains 3% sucrose) | 1 package |
| 100X Vitamin Supplement: 10 mg/l thiamine 50 mg/l pyridoxine 50 mg/l nicotinic acid | 10 ml |
| 1 mg/ml NAA (napthaleneacetic acid) stock | 0.1 ml |
| 1 mg/ml BAP stock | 1.0 ml |
| agar | 8.0 g |
| pH 5.8 | |
| Root Induction Medium (MX$^-$) | |
| Murashige's Minimal Organics Medium GIBCO #510-1118 (contains 3% sucrose) | 1 package |
| 100X Vitamin Supplement: 10 mg/l thiamine 50 mg/l pyridoxine 50 mg/l nicotinic acid | 10 ml |
| agar | 8.0 g |
| pH 5.8 | |

A. Construction of plasmids for integration and expression of the cre coding region in plant cells

EXAMPLE 1

The starting material for construction of Cre/Hpt-A was the plasmid pK35CAT, which is described in Lin et al., Plant Physiology, 84: 856–861 (1987) and has been deposited in the ATCC and bears deposit accession number 68174. This plasmid contains a CaMV 35S promoter (35S/P) directing expression of the chloramphenicol acetyltransferase (CAT) coding region and followed by a nopaline synthase (NOS) gene polyadenylation nucleotide sequence (NOS 3'). pK35CAT was derived from pK35K, which was in turn derived from pKNK. pKNK has been deposited with the ATCC and bears the deposit accession number 67284. pKNK is a pBR322 based vector which contains a neomycin phosphotransferase II (NptII) promoter fragment, a nopaline synthase (NOS) promoter fragment, the coding region of NptII and the polyadenylation region from the NOS gene. A map of this plasmid is shown in Lin et al., Plant Physiol. 84: 856–861 (1987). The 320 bp ClaI-BglII fragment in pKNK that contains the NptII promoter was obtained as a HindIII-BglII fragment from the NptII gene of the transposon Tn5 described by Beck et al., Gene 19: 327–336 (1982). The HindIII site was converted to a ClaI site by linker addition. The NptII promoter fragment is followed by a 296 bp Sau3A-PstI NOS promoter (NOS/P) fragment corresponding to nucleotides −263 to +33, with respect to the transcription start site, of the NOS gene described by Depicker et al., J. Appl, Genet, 1: 561–574 (1982). The PstI site at the 3' end was created at the translation initiation codon of the NOS gene. The NOS/P is followed by a 998 bp HindIII-BamHI sequence containing the NptII coding region obtained from the transposon Tn5 [Beck et al., Gene 19: 327–336 (1982)] by the creation of HindIII and BamHI sites at nucleotides 1540 and 2518, respectively. The NptII coding region is then followed by a 702 bp BamHI-ClaI fragment containing the 3' end of the nopaline synthase gene including nucleotides 848 to 1550 [Depicker et al., J. Appl. Genet. 1: 561–574 (1982)]. The remainder of pKNK consists of pBR322 sequences from 29 to 4361.

pKNK was converted to pK35K by removing the NptII and NOS promoters and replacing them with a CaMV 35S promoter. The EcoRI-HindIII 35S promoter fragment is the same as that contained in pUC35K which has been deposited with the ATCC and bears the deposit accession number 67285. The 35S promoter fragment was prepared as follows, and as described in Odell et al., Nature 313: 810–813 (1985) except that the 3' end of the fragment includes CaMV sequences to +21 with respect to the transcription start site. A 1.15 kb BglII segment of the CaMV genome containing the region between −941 and +208 relative to the 35S transcription start site was cloned in the BamHI site of the plasmid pUC13. This plasmid was linearized at the SalI site in the polylinker located 3' to the CaMV fragment and the 3' end of the fragment was shortened by digestion with nuclease Ba131. Following the addition of HindIII linkers, the plasmid DNA was recircularized. From nucleotide sequence analysis of the isolated clones, a 3' deletion fragment was selected with the HindIII linker positioned at +21. To create pK35K this 35S promoter fragment was isolated as an EcoRI-HindIII fragment, the EcoRI site coming from the polylinker of pUC13, and ligated to pKNK that had been digested with EcoRI and HindIII, the EcoRI site lying 5' to the ClaI site in pBR322.

pK35K was converted to pK35CAT by dropping out the NptII coding region and replacing it with the coding region of chloramphenicol acetyl transferase (CAT) as mapped and described in Lin et al., Plant Physiol. 84: 856–861 (1987). The CAT coding region was obtained as a 975 bp Sau3A fragment from pBR325. The ends were filled in and the fragment was ligated into a filled in SalI site of pGEM2. A clone, pGCAT9, was selected that contains the insert oriented such that the HindIII and BamHI sites of the polylinker are located 5' and 3' to the CAT coding region, respectively. The CAT coding region was isolated from this clone by HindIII and BamHI digestion, and ligated into HindIII and BamHI digested pK35K. The resultant construction, termed pK35CAT, also contains the NOS 3' fragment which remains unaltered in the conversion of pKNK to pK35K, and finally to pK35CAT.

The entire cre gene was originally obtained from the genome of bacteriophage P1 on an EcoRI fragment as described by Sternberg and Hamilton, *J. Mol. Biol*, 150: 467–486 (1981). The cre coding region was prepared as an XhoI-EcoRI fragment in plasmid pRH103A6 as described by Sternberg et al., *J. Mol. Biol.* 187: 197–212 (1986). The XhoI site was added as a linker following Bal31 deletion of the sequence 5' to the cre coding region, resulting in the placement of the XhoI site approximately 50 bp 5' to the translation initiation ATG. The EcoRI site was added as a linker following Bal31 deletion of the sequence 3' to the cre coding region, resulting in the placement of the EcoRI site approximately 100 bp 3' to the translation stop codon. The 3' EcoRI site was then replaced with a SalI site generating pBS7 as described in Sauer, *Mol. and Cell. Biol*, 7: 2087–2096 (1987) so that the cre coding region could be isolated as a XhoI-SalI fragment. This cre coding fragment is the same as that present in plasmid pBS39 which has been deposited with the ATCC and bears deposit accession number 53255. The XhoI-SalI cre coding region fragment was isolated, HindIII linkers were added to the ends, and it was ligated with HindIII digested pK35CAT, generating pK35CreCAT. This plasmid contains a chimeric 35S/P-cre-CAT-NOS 3' gene.

To construct Cre/Hpt-A, pK35CAT was digested with BamHI, the end was partially filled with dGTP and dATP according to the method of Hung and Wensink, *Nucl. Acids Res.* 12: 1863–1874 (1984) and then it was digested with HindIII to remove the CAT coding region. The HindIII-SalI DNA fragment containing the cre coding region was isolated from pK35CreCAT, whose construction is described in the previous paragraph, and the SalI site was partially filled with dCTP and dTTP during its preparation. This cre coding region fragment was then ligated into the prepared vector derived from pK35CAT creating the plasmid pK35Cre which contains a chimeric 35S promoter-cre coding region-NOS 3' gene.

EXAMPLE 2

Next a ClaI-SalI fragment containing a chimeric NOS/P-Hpt-NOS 3' gene (Hpt=hygromycin phosphotransferase) and the NptI gene (neomycin phosphotransferase I) was isolated from pAGS122 which is analogous to pAGS120 that is described in van den Elzen et al., *Plant Molecular Biology* 5: 299–302 (1985). A SalI linker was added to the ClaI end of the fragment and it was ligated into SalI digested pK35Cre creating the plasmid Cre/Hpt-A which is shown in FIG. 1A.

The boxes represent the chimeric 35S/P-cre-NOS 3' and NOS/P-Hpt-NOS 3' chimeric genes. The arrows represent the transcripts expressed by these chimeric genes. The NptI gene is derived from Tn903. These genes are incorporated in a pBR322 vector.

EXAMPLE 3

The starting material for construction of Cre/Hpt-B was the plasmid pDH51 that was described by Pietrzak et al., *Nucleic Acids Research*, 14: 5857–5868 (1986). This plasmid contains a CaMV 35S promoter including sequences between 6909 and 7437 of the CaMV genome and a CaMV polyadenylation nucleotide sequence including sequences between 7439 and 7632, separated by several restriction enzyme sites, including XbaI. The CaMV promoter fragment in pDH51 was prepared by adding an EcoRI linker 5' to the NcoI site at 6909 of the CaMV genome and a KpnI linker at the HphI site at 7437. The polyadenylation region fragment was prepared by adding an SphI linker at the HphI site at 7439 and a HindIII linker following KpnI, SstI, and EcoRI sites that had been added onto position 7632 during a cloning step in pUC18. Both of these fragments were cloned into pUC18 using the restriction sites located on their ends to generate pDH51. In the resulting plasmid, EcoRI sites are located on either end outside of the CaMV promoter and 3' region. pDH51 was digested with XbaI and the ends were partially filled with dCTP and dTTP. The HindIII DNA fragment containing the cre coding region was isolated from pk35CreCAT and the ends were partially filled with dATP and dGTP, then ligated into the prepared pDH51 vector. To identify a plasmid with the HindIII cre fragment in the proper orientation for expression, a SalI digest was done. The desired plasmid was digested with SalI since the SalI site at the 3' end of the cre fragment is adjacent to the SalI site at the 5' end of the CaMV 3' region. A BamHI digest confirmed the correct orientation: a 430 bp fragment between the BamHI site at the 3' end of the 35S/P region and a BamHI site within the cre coding region was present. The resulting pDH51Cre plasmid contains a chimeric 35S promoter-cre coding region-CaMV 3' gene.

EXAMPLE 4

Next the entire chimeric gene was cloned into pJJ2644, which is a binary vector for *Agrobacterium tumefaciens* transformation that carries a chimeric 1'/P-Hpt-NOS 3' gene, a tetracycline resistance gene, a broad host range origin of replication, and T-DNA borders. pJJ2644 has been deposited with the ATCC and bears deposit accession number 68178 and was constructed as follows. The broad host range plasmid pRK290 that was described by Ditta et al., *Proc. Natl. Acad. Sci, USA* 77: 7347–7351 (1980) served as the basic vector. This plasmid was cut with EcoRI, the ends filled, and it was ligated to an end site filled EcoRI-HindIII fragment isolated from pAGSIII creating pJJ1881. The fragment from pAGSIII contains the left and right border fragments from the *Agrobacterium tumefaciens* T-DNA located on either side of a chimeric NptII gene and its construction is described in van den Elzen et al., *Plant Molec. Biol*, 5: 149–154 (1985). The ClaI-BamHI chimeric NptII gene fragment was replaced with the ClaI-BamHI fragment from pBR322, thereby adding a HindIII site. To create pJJ2501 a HindIII-ClaI fragment was added that contains a chimeric 1'/P-Hpt-NOS 3' gene consisting of the 1' promoter described by Velten et al., *EMBO J.* 12: 2723–2730 (1984), the Hpt coding region described by van den Elzen et al., *Plant Molec. Biol*, 5: 299–302 (1985), from which the ATG sequence located just 5' to the translation initiation ATG had been removed, and the NOS 3' region. Next the XhoI site located outside of the T-DNA borders was deleted. Between the BamHI and HpaI sites, located 3' to the chimeric Hpt gene, a linker, including sites for BamHI, XbaI, HindIII, XhoI, EcoRI, and HpaI, was added creating pJJ2644.

Figure 1B:
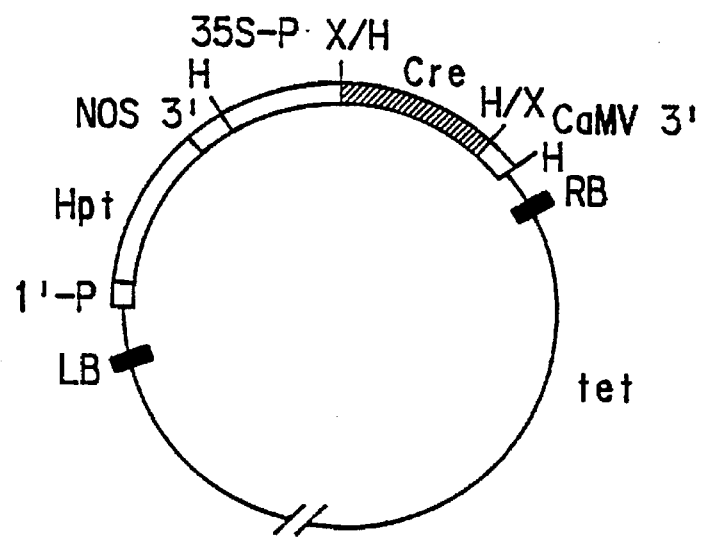
FIG. 1B shows the map of plasmid Cre/Hpt-B. Restriction sites used in making the construction are marked as B: BamHI, C: ClaI, E: EcoRI, H: HindIII, P: PstI, S: SalI and X: XbaI.

This vector was digested with HindIII and ligated to the HindIII linkered EcoRI fragment from pDH51Cre containing the chimeric cre gene. The resulting plasmid is Cre/Hpt-B which is shown in FIG. 1B. The boxes represent the chimeric 35S/P-cre-CaMV 3' and 1'/P-Hpt-NOS 3' genes.

The T-DNA left and right borders are marked as filled boxes. The slashes indicate unrepresented sequences of the binary vector PJJ2644, which includes a tetracycline resistance gene (tet).

A plasmid used as a control is called -/Hpt-B and is the pJJ2644 vector with no chimeric cre gene added.

B. Construction of plasmids containing the lox site for integration and analysis in plant cells

EXAMPLE 5

The starting material for construction of loxP/NptII/Hra was the plasmid pBS69 containing two loxP sites which is described by Sauer and Henderson, *Nucleic Acids Research*, 17: 147–161 (1989). The loxP site was originally obtained from the bacteriophage P1 genome on a BamHI fragment cloned in pBR322 as described by Abremski et al., *Cell* 32: 1301–1311 (1983). This reference also describes construction of an 80 bp EcoRI-HindIII fragment containing loxP made by adding an EcoRI linker to the BclI site and a HindIII linker to the PvuII site, located on either side of loxP. A 50 bp BamHI-XhoI fragment containing loxP was made by deleting in from the BclI site with Ba131 and adding a BamHI linker 10 bp from loxP, and deleting in from the PvuII site and adding an XhoI linker 6 bp from loxP. The 80 bp EcoRI-HindIII fragment containing loxP was ligated between the EcoRI and HindIII sites in the pBR322 plasmid containing the 50 bp loxP fragment resulting in the plasmid pRH42 that has two loxP sites oriented in the same direction. A derivative of this plasmid called pRH43 having the NptII gene from Tn5 between the loxP sites is also described. A derivative of pRH43 called pRH499 that has the Leu2 gene of yeast between the loxP sites is described and a map shown in Sauer, *Mol. and Cell. Biol.* 7: 2087–2096 (1987). As described in this reference, the HindIII site adjacent to the 80 bp lox site was deleted generating pBS30. pBS30 carries the same EcoRI-XhoI fragment containing two directly oriented loxP sites that is present in pBS44 which has been deposited with the ATCC and bears deposit accession number 53254. As described in Sauer and Henderson [*Nucl. Acids Res.* 17: 147–161 (1989)]pBS69 was generated from pBS30 by replacing the 80 bp HindIII-SalI fragment containing the loxP site with the 50 bp HindIII-XhoI fragment containing the loxP site. This was done to remove extra sequence in the 80 bp fragment that contained ATG translation initiation codons. Thus pBS69 has two directly oriented 50 bp loxP containing fragments surrounding a yeast Leu2 gene.

Part of the Leu2 gene was removed using the EcoRI site located within the Leu2 gene and the BamHI site adjacent to one loxP site, and replaced with a polyadenylation nucleotide sequence (polyA) derived from the tobacco Rubisco small subunit gene described by Mazur and Chui [*Nucleic Acids Research*, 13: 2373–2386 (1985)]. This reference describes the cloning and sequencing of this gene. The BamHI-XbaI fragment containing the sequence region between 1905 and 2289 was isolated, the XbaI site being filled in during its preparation. pBS69 was digested with EcoRI, the end filled in, then digested with BamHI. The ligation of these two DNAs resulted in the plasmid pBS69polyA.

EXAMPLE 6

Next an XhoI-HindIII fragment containing the loxP-polyA-loxP region was isolated and a HindIII linker was added to the XhoI end. This fragment was ligated into HindIII digested pKNK. The construction of pKNK was described in Example 1 and it contains the NOS promoter joined to the NptII coding region by a HindIII site resulting in a chimeric gene which confers kanamycin resistance to plant cells. The orientation of the loxP-polyA-loxP HindIII insert was determined by digestion with BamHI. The plasmid with the HindIII fragment inserted such that the polyA site has the same orientation as the NOS/P and the NptII coding region was called pKNKloxA. It was anticipated that the polyadenylation nucleotide sequence located between the NOS/P and NptII coding region would block production of a viable NptII transcript thereby causing transformed cells to retain their kanamycin sensitivity.

Next a PstI fragment that contains the Hra (sulfonylurea resistant acetolactate synthase) gene derived from pALS032BV that is described by Lee et al. [*EMBO J.* 7: 1241–1248 (1988)], and also contains a HindIII fragment with a streptomycin/spectinomycin resistance gene derived from the R100.1 plasmid and described by Prentki and Krisch, *Gene*, 29: 303–313 (1984) was added. This fragment was constructed by adding SalI linkers to the HindIII ends of the isolated strep/spec fragment and ligating it into the SalI site adjacent to the Hra gene in pALS032BV. The PstI fragment was then isolated, the ends filled in, and it was ligated into SalI digested and filled pKNKloxA. The resulting plasmid called loxP/NptII/Hra is shown in FIG. 1C and has been deposited with ATCC (American Type Culture Collection, 12301 Parklawn Drive, Rockville, Md. 20852) on 16 Nov. 1989 as ATCC accession number 68177.

Figure 1C:
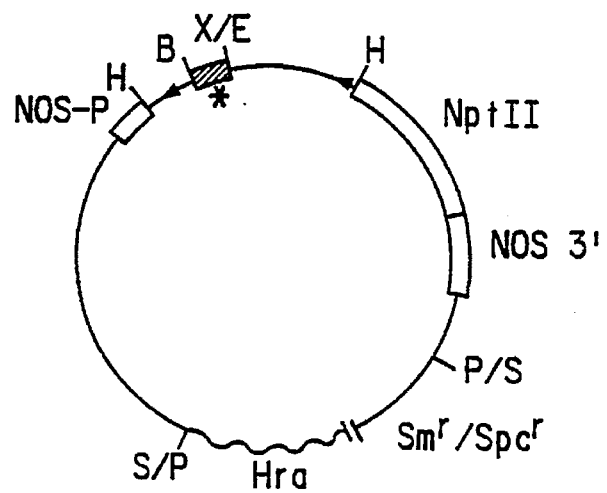
FIG. 1C shows the map of plasmid loxP/NptII/Hra. Restriction sites used in making the construction are marked as B: BamHI, C: ClaI, E: ECoRI, H: HindIII, P: PstI, S: SalI and X: XbaI.

In FIG. 1C, the open boxes represent the chimeric NOS/P-NptII-NOS 3' gene that is interrupted between the promoter and coding region by a Rubisco small subunit gene polyadenylation region, shown as the stipled box, which is surrounded by two loxP sites, represented by arrows showing that the loxP sites are in the same orientation. The asterisk marks the polyadenylation site. The plasmid includes the sulfonylurea-resistant ALS gene called Hra and the streptomycin and spectinomycin resistance marker, incorporated in a pBR322 vector. The orientation of the PstI insert was not determined.

C. Transformation of tobacco with the cre coding region

The chimeric 35S/P-Cre-NOS 3' gene, described in Examples 1 and 2, was introduced into tobacco by *Agrobacterium tumefaciens* infection of tobacco leaf disks. Primary transformants were analyzed to demonstrate the presence of the cre coding region and expression of the cre mRNA in tobacco cells as well as expression of the linked Hpt gene which confers hygromycin resistance.

The plasmid Cre/Hpt-A was transferred into *A. tumefaciens* by a method involving a three-way mating that was essentially as described by Fraley et al. [*Proc. Natl. Acad. Sci, USA*, 80: 4803–4807 (1983)] except for the following points. Cre/Hpt-A was mated into Agrobacterium strain GV3850 that was described by Zambryski et al. [*J. of Mol. and Appl. Genetics*, 1: 361–370 (1982)]. Colonies from the Cre/Hpt-A mating were selected on LB plates containing 100 µg/ml rifampicin and 25 µg/ml kanamycin. Selected colonies were confirmed as cointegrates of the Cre/Hpt-A plasmid into the Ti plasmid by Southern blot analyses.

Standard aseptic techniques for the manipulation of sterile media and axenic plant/bacterial cultures were followed, including the use of a laminar flow hood for all transfers. Potted tobacco plants for leaf disk infections were grown in a growth chamber maintained for a 14 hr, 24° C. day, 10 hr, 20° C. night cycle, with approximately 80% relative humidity, under mixed cool white fluorescent and incandescent lights. Tobacco leaf disk infection was carried out essentially by the method of Horsch et al. [*Science* 27, 1229–1231 (1985)], omitting nurse cultures, as described below.

Healthy young tobacco leaves were harvested, surface sterilized, and rinsed as described in Materials and Methods. Leaf disks, 8 mm in diameter, were prepared from whole leaves using a sterile paper punch.

Leaf disks were inoculated by submerging them for several minutes in 20 ml of a 1:20 dilution of the overnight culture of Agrobacterium harboring the cointegrate Cre/Hpt-A Ti plasmid. The culture was started by inoculating 5 mls of YEB broth (Table 1) with a single bacterial colony. The culture was grown for approximately 17–20 hours in 18 mm glass culture tubes in a New Brunswick platform shaker maintained at 28° C.

After inoculation, the leaf disks were placed on 0.1N1B agar medium (Table 2) in petri dishes which were then sealed with parafilm. The petri dishes were incubated under mixed fluorescent and "Gro and Sho" plant lights (General Electric) for 2–3 days in a culture room maintained at approximately 25° C.

To rid the leaf disks of Agrobacterium and to select for the growth of transformed tobacco cells, the leaf disks were transferred to fresh 0.1N1B medium containing 500 mg/L cefotaxime and 10–20 mg/l hygromycin. Cefotaxime was kept as a frozen 200 mg/ml stock solution and added aseptically (filter sterilized through a 0.45 µm filter) to the media after autoclaving. A fresh hygromycin stock (20 mg/ml) was made for each use and was filter sterilized into the autoclaved media. Leaf disks were incubated under the growth conditions described above for 3 weeks and then transferred to fresh media of the same composition.

Approximately 1 month later, shoots developing on hygromycin-containing medium were excised with a sterile scalpel and planted in MX⁻ medium containing 200 mg/L cefotaxime and 10 mg/L hygromycin. Root formation was recorded within 3 weeks.

Leaves were removed from the rooted excised shoots to determine levels of resistance to hygromycin in a callus induction assay on selective media. To induce callus formation, leaves were excised and leaf disks, 8 mm in diameter, were made using a sterile paper punch and planted on callus induction medium containing 20 and 50 mg/l hygromycin. Callus growth on selective and non-selective media was recorded within 3 weeks.

The results shown in Table 3 indicate that transformation of tobacco had been achieved with Agrobacterium harboring the Cre/Hpt-A Ti plasmid, based on production of hygromycin resistant callus. All ten transformants tested were resistant to hygromycin. Primary transformants were analyzed by molecular techniques to verify the presence of the cre mRNA sequences. Seven independent tobacco plants transformed with Cre/Hpt-A were assayed for expression of the chimeric cre gene by Northern blots as described in Materials and Methods. The probe used to hybridize to the filter containing the RNA prepared from each plant was a BamHI-ClaI DNA fragment that was isolated from the pK35K or pKNK plasmid, which are both described in Example 1. This fragment contains the NOS polyadenylation nucleotide sequence which includes a region of untranslated transcribed sequence. Since both the 35S/P-Cre-NOS 3' and NOS/P-Hpt-NOS 3' genes have homology to this probe, the transcript from each gene is detected in this experiment. The expected 2.0 kb transcript from the cre gene and the expected 1.5 kb transcript from the Hpt gene were detected on the Northern filter. All of the plants assayed, except for one, produced a detectable level of Cre transcript indicating the presence and expression of the chimetic cre gene in the plant cells.

Plants exhibiting hygromycin resistance were transferred to soil and grown to maturity in a growth chamber as described above. Individual inflorescences were covered with bags to permit self-fertilization without cross-pollination. Mature seeds were harvested and progeny tests were conducted to determine the inheritance of the introduced Cre/Hpt DNA. Inheritance was monitored by following the hygromycin resistance trait.

Seed was surface sterilized for 30 minutes in 10% commercial bleach and 1% SDS with intermittent mixing, rinsed 3–5 times with sterile deionized water, dried, and planted on MX⁻ medium in the presence or absence of 50 mg/l hygromycin. Sensitive seeds germinated, but did not develop further. A segregation ratio of 3 resistant progeny to 1 sensitive indicated the presence of a single site of integration of the hygromycin resistance gene into the genome of the transformant, which was then stably inherited by its progeny. This was seen in seven out of eight independent transformants tested. The eighth transformant exhibited a ratio which was greater than 3:1, indicating the presence of more than one integration site.

TABLE 3

Callus Growth on Hygromycin

| ID | WEIGHT IN GRAMS Hygromycin Concentration | | |
|---|---|---|---|
| | 0 mg/l | 20 mg/l | 50 mg/l |
| U1 | 9.02 | 4.55 | 3.36 |
| U2a | 8.88 | 2.34 | 2.43 |
| U2b | 7.72 | 3.77 | 2.88 |
| U2c | 3.69 | 1.32 | 0.85 |
| C1 = U3a[1] | 4.43 | 2.42 | 1.28 |
| C2 = U3b[1] | 8.32 | 3.63 | 2.02 |
| U4a[1] | 6.21 | 2.52 | 1.15 |
| C3 = U4b | 5.80 | 2.94 | 2.82 |
| U5 | 4.23 | 3.28 | 2.49 |
| U6a[1] | 5.79 | 2.16 | 2.00 |
| C4 = U6b | 5.52 | 2.40 | 1.42 |
| U6c | 11.37 | 2.56 | 2.10 |
| C5 = U7a | 8.41 | 2.78 | 2.16 |
| C6 = U7b | 5.22 | 4.66 | 4.23 |
| U7c | 8.52 | 3.38 | 2.88 |
| U8 | 4.38 | 5.15 | 2.09 |
| WT | 3.55 | 0.68 | 0.36 |

[1]Weight in grams is the average of results from two callus induction assays done with the same transformant D. Production of plant cells and plants with two loxP sites integrated into the genome The loxP-polyA-loxP DNA sequence described in Examples 5 and 6 was introduced into tobacco by Agrobacterium tumefaciens infection of tobacco leaf disks as described in Materials and Methods. Primary transformants were analyzed to demonstrate the presence of the loxP-polyA DNA sequence in the tobacco cells as well as expression of the linked Hra gene which confers resistance to chlorsulfuron.

The plasmid loxP/NptII/Hra was transferred into A. tumefaciens by a method involving a three-way mating that was essentially as described by Fraley et al. [Proc. Natl. Acad. Sci. USA, 80, 4803–4807 (1983)] except for the following points. LoxP/NptII/Hra was mated into Agrobacterium strain GV3850 that was described by Zambryski et al. [J. of Mol. and Appl. Genetics, 1: 361–370 (1982)]. Colonies from the loxP/NptII/Hra mating were selected on 100 µg/ml rifampicin and 100 µg/ml each of spectinomycin and streptomycin. Selected colonies were confirmed as cointegrates of the loxP/NptII/Hra plasmid into the Ti plasmid by Southern blot analyses.

Tobacco leaf disks were obtained, inoculated with *A. tumefaciens* harboring the cointegrate loxP/NptII/Hra plasmid, and incubated on 0.1N1B as described in Materials and Methods.

To rid the leaf disks of Agrobacterium and to select for the growth of transformed tobacco cells, the leaf disks were transferred to fresh 0.1N1B medium containing 500 mg/l cefotaxime and 20–2.00 ppb chlorsulfuron. Cefotaxime was kept as a frozen 200 mg/ml stock solution and added aseptically (filter sterilized through a 0.45 μm filter) to the media after autoclaving. A fresh chlorsulfuron stock was prepared for each use by first making a 0.2 mg/ml solution in 0.01N $NH_4OH$, which was then diluted 1:10 with deionized water, and filter sterilized into the autoclaved media. Leaf disks were incubated under the growth conditions described above for 3 weeks and then transferred to fresh media of the same composition.

Approximately 1 month later, shoots developing on medium containing 20–50 ppb chlorsulfuron were excised with a sterile scalpel and planted in $MX^-$ medium containing 200 mg/l cefotaxime and 20 mg/l chlorsulfuron. Root formation was recorded within 3 weeks.

Leaves were removed from the rooted excised shoots to determine levels of resistance to chlorsulfuron and kanamycin in a callus induction assay on selective media. To induce callus formation, leaves were excised and leaf disks, 8 mm in diameter, were made using a sterile paper punch and planted on callus induction medium containing 5, 10, or 20 ppb chlorsulfuron and on callus induction medium containing 100 mg/l kanamycin. Callus growth on selective and non-selective media was recorded at 3 weeks. Twenty-one independent transformants tested were resistant to chlorsulfuron. All but one retained sensitivity to kanamycin.

Figure 2A:
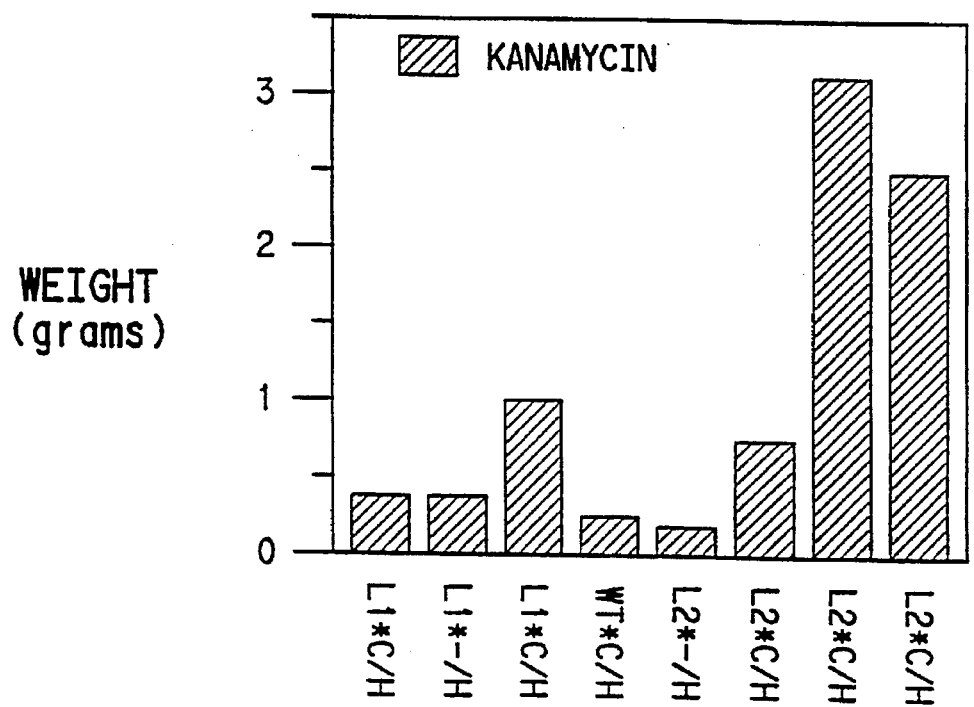
FIG. 2A illustrates the results of a callus induction assay, demonstrating site-specific recombination in loxP plants re-transformed with *Agrobacterium tumefaciens* harboring the Cre/Hpt-B vector.

The results shown in Table 4 indicate that transformation of tobacco had been achieved with the Agrobacterium harboring the loxP/NptII/Hra Ti plasmid based on production of chlorsulfuron resistant callus. Since the cells generally remain kanamycin sensitive, these data also suggest that no viable transcript containing the NptII sequence is produced. Nine independent tobacco plants transformed with loxP/NptII/Hra were assayed for the presence of the loxP-polyA DNA region by Southern blots as described in Materials and Methods. The probe used to hybridize to the filter containing BamHI digested DNA prepared from each plant was a HindIII-BamHI DNA fragment that was isolated from the pK35K plasmid. This fragment contains the coding region for NptII and is shown in the diagram in FIG. 2B. In DNA of each of the nine loxP plants assayed the 2.4 kb BamHI fragment containing the polyadenylation nucleotide sequence and a loxP site, as diagrammed in FIG. 2B, was detected as shown in FIG. 2C lanes 1 and 6. None of the loxPplants had the 5.7 kb fragment shown in FIG. 2B indicating that no excision could be detected in these primary transformants.

Figure 2B:
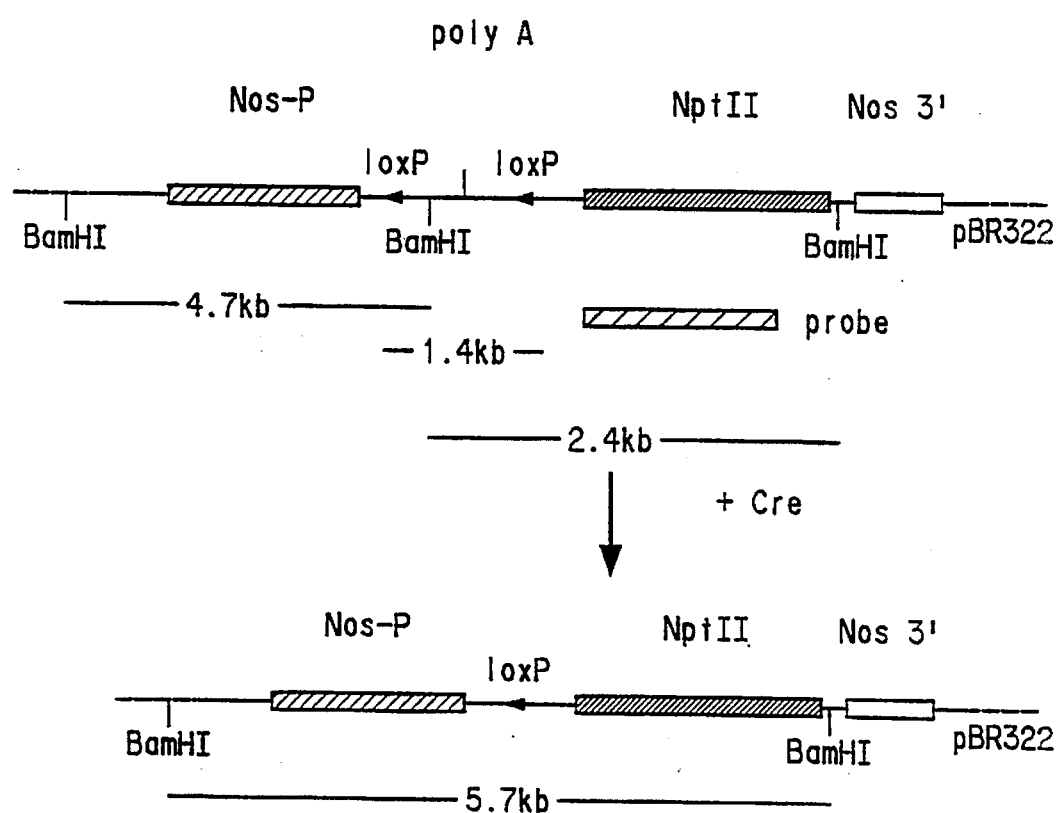
FIG. 2B is a map of the lox region of the loxP/NptII/Hra vector.
Figure 2C:
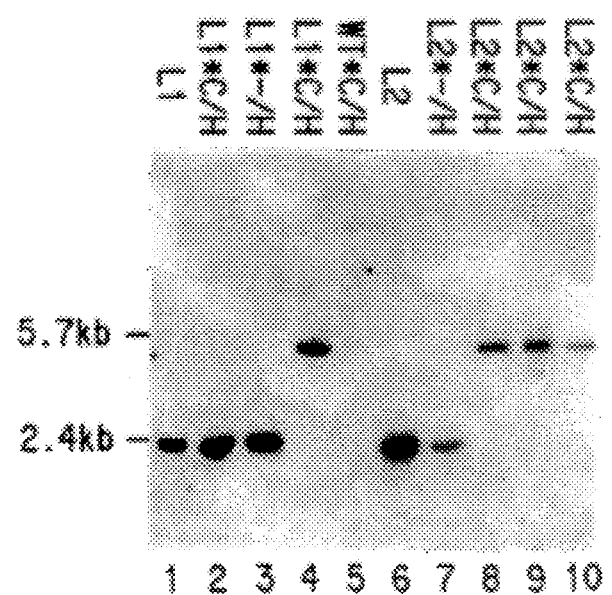
FIG. 2C shows a Southern blot analysis of plants re-transformed with *Agrobacterium tumefaciens* harboring the Cre/Hpt-B vector.

In FIG. 2B, distances between the BamHI sites and between the loxP sites in the original construction are shown above. Below is a map of the expected confirguration following recombination between loxP sites, with the loss of a BamHI site and resulting change in distance between remaining BamHI sites shown. The 2.4 kb and 5.7 kb fragments marked in bold are those detected by the probe shown as a checkered box.

Plants exhibiting chlorsulfuron resistance were transferred to soil and grown to maturity in a growth chamber as described above. Individual inflorescences were covered with bags to permit self-fertilization without cross-pollination. Mature seeds were harvested and progeny tests were conducted to determine the inheritance of the inserted DNA fragments. Inheritance was monitored by following the linked chlorsulfuron resistance trait.

Seed was surface sterilized for 30 minutes as described above, dried, and planted on $MX^-$ medium in the presence or absence of chlorsulfuron or kanamycin. Kanamycin was used to assay for the stability of the inactivated NptII gene. Sensitive seeds germinated, but did not develop further. A segregation ratio of 3 chlorsulfuron resistant progeny to 1 sensitive indicated the presence of a single site of integration of the Hra gene in the genome of the transformant, which was then stably inherited by its progeny. This was seen in 6 out of 20 independent transformants tested. Higher ratios of resistant to sensitive progeny, exhibited by 14 out of 20 of the transformants, indicated insertions at multiple positions in the genome. For example, a 15/1 ratio indicates the presence of insertions at two unlinked loci and a 255/1 ratio indicates insertions at four unlinked loci in the transformants.

TABLE 4

Callus Growth on Chlorsulfuron and Kanamycin

| | WEIGHT IN GRAMS | | |
|---|---|---|---|
| ID | No Selection | 10 mg/l Chlorsulfuron | 100 mg/l Kanaymcin |
| Q1 | 6.99 | 4.93 | 0.31 |
| L1 = Q3 | 8.19 | 3.54 | 0.48 |
| L2 = Q8 | 4.18 | 2.41 | 0.28 |
| Q9 | 2.58 | 5.78 | 0.32 |
| L3 = Q10 | 6.09 | 6.04 | 0.42 |
| Q11 | 9.87 | 10.19 | 0.40 |
| Q12 | 3.60 | 4.13 | 0.31 |
| Q14 | 7.57 | 3.15 | 0.36 |
| L4 = Q15 | 4.69 | 13.98 | 0.27 |
| Q16 | 3.98 | 4.92 | 0.36 |
| L5 = Q17 | 4.92 | 8.12 | 0.38 |
| Q23 | 5.75 | 4.94 | 0.33 |
| Q25 | 8.32 | 8.75 | 0.31 |
| Q26 | 5.30 | 11.60 | 1.10 |
| Q27 | 5.33 | 7.38 | 0.31 |
| L6 = Q29 | 13.28 | 4.86 | 0.41 |
| Q30 | 6.48 | 6.52 | 0.35 |
| Q31 | 7.66 | 12.35 | 0.31 |
| Q32 | 14.41 | 7.62 | 0.37 |
| WT | 15.48 | 0.50 | 0.90 |

E. Re-transformation of loxP plants with the cre coding region

The binary vector plasmid Cre/Hpt-B, described in Example 4, was introduced into transgenic tobacco plants, having two loxP sites already integrated in the genome, by *A. tumefaciens* infection of tobacco leaf disks from loxP primary transformants. Re-transformed plants were analyzed to demonstrate site-specific recombination at the loxP sites.

The procedures described in Materials and Methods were followed, except healthy leaves were harvested from transgenic loxP tobacco plants growing in Magenta GA7 vessels (Magenta Corp., Chicago, Ill., USA). These plants were produced as in Section D. Leaf disks, 8 mm in diameter, were prepared from these axenic leaves using a sterile paper punch. To select for the growth of transformed tobacco cells and to rid the leaf disks of Agrobacterium, a group of leaf disks were transferred to fresh 0.1N1B medium containing 10–20 mg/L hygromycin and 500 mg/l cefotaxime. To select for site-specific recombination at the loxP sites in transformed tobacco cells and to rid the leaf disks of Agrobacterium, another group of leaf disks were transferred to fresh 0.1N1B medium containing 100 mg/l kanamycin and 500 mg/l cefotaxime. Cefotaxime was kept as a frozen 200 mg/ml stock solution and added aseptically (filter sterilized through a 0.45 μm filter) to the media after autoclaving. Fresh hygromycin stock (20 mg/ml) and kanamycin stock (50 mg/l) was made for each use and was filter sterilized into the autoclaved media. Leaf disks were incubated under the growth condition described above for 3 weeks and then transferred to fresh media of the same composition.

Approximately 1 month later, shoots developing on hygromycin-containing medium were excised with a sterile scalpel and planted in MX⁻ medium containing 200 mg/l cefotaxime and 10 mg/l hygromycin in Magenta GA7 vessels. Shoots developing on kanamycin-containing medium were excised with a sterile scalpel and planted in MX⁻ medium containing 200 mg/l cefotaxime and 100 mg/l kanamycin in Magenta GA7 vessels.

Leaves were removed from the rooted excised shoots to determine levels of resistance to hygromycin and kanamycin in a callus induction assay on selective media. To induce callus formation, leaves were excised and leaf disks, 8 mm in diameter, were made using a sterile paper punch and planted on callus induction medium containing 30 mg/l hygromycin and on 50 mg/l kanamycin. Callus growth was recorded at 3 weeks.

The results shown in FIG. 2A indicate that Cre-mediated site-specific recombination of the loxP sites in the tobacco genome had been achieved following re-transformation of the loxP plants with the Agrobacterium harboring the Cre/Hpt-B plasmid, based on production of kanamycin resistant callus. Recombination resulting in excision of the polyA site located between the NOS/P and NptII coding region, allowed production of a viable NptII transcript conferring kanamycin resistance to the cells. Only leaf disks from loxP plants re-transformed with the Cre/Hpt-B vector formed callus on medium containing kanamycin. Plants from the transformation of wild type tobacco, with either –/Hpt-B or with Cre/Hpt-B, were all kanamycin sensitive. Three loxP re-transformants from the –/Hpt-B inoculation were also kanamycin sensitive.

In FIG. 2A, each bar represents the total weight of five leaf disks grown on callus induction medium (Table 2) containing 50 mg/l kanamycin. Weight includes that of the original leaf disks, which account for weights up to 0.4 grams. Disks were taken from hygromycin selected plants resulting from re-transformation of loxP plants: L1 and L2 or untransformed tobacco plants: WT, with either the cre gene: Cre/Hpt-B vector (i.e., L1*C/H or L2*C/H), or without the cre gene: –/Hpt-B vector (i.e., L1*–/H or L2*–/H). All plants exhibited growth on hygromycin.

Plants resulting from re-transformation of loxP plant tissue with Cre/Hpt-B were analyzed by Southern blots to detect recombination. The same NptII fragment probe described in Section D was hybridized to filters containing BamHI digested DNA isolated from re-transformants. Of the five loxP*Cre re-transformant plant DNAs analyzed, one retained the 2.4 kb fragment detected in loxP primary transformants and in the other four a new 5.7 kb fragment was detected, as shown in FIG. 2C lanes 4, 8, 9 and 10. In this figure, lanes contain approximately 10 μg of BamHI digested DNA from the same plants described in (A), in the same order, except that lanes 1 and 6 contain additional samples from the original L1 and L2 plants, respectively. Positions of the 2.4 kb and 5.7 kb bands detected with the NptII probe, as described in (b), are marked. The absence of the 2.4 kb fragment and the presence of the 5.7 kb fragment in these re-transformants indicated that recombination had occurred between the two loxP sites as diagrammed in FIG. 2B: excision results in the loss of a BamHI site located between the two loxP sites so that the distance between adjacent BamHI sites is increased. The one loxP*Cre re-transformant that retained the 2.4 kb fragment, as shown in FIG. 2C lane 2, also retained sensitivity to kanamycin, as shown in FIG. 2A, demonstrating consistency between the Southern blot analysis and the phenotypic response. DNAs from two control loxP plants re-transformed with –/Hpt contained the 2.4 kb unrecombined fragment as shown in FIG. 2C lanes 3 and 7, indicating that recombination is dependent on the presence of Cre. The wild type control plant showed no hybridization to the probe as shown in FIG. 2C lane 5.

F. Genetic crosses of heterozygous loxP and Cre plants

A method utilized to produce excisional recombination was to genetically unite the Cre recombinase with the loxP-polyA-loxP DNA sequence, which is integrated in the plant genome, by sexual hybridization of loxP and Cre plants. In this example, primary transformants obtained by tobacco leaf disk transformation, as described in Sections C and D, were utilized.

Primary transformants were transferred to soil and grown in a growth chamber maintained for a 14 hr, 24° C. day, 10 hr, 20° C. night cycle, with approximately 80% relative humidity, under mixed cool white fluorescent and incandescent lights. Plants were grown to maturity and hand pollinations were performed using a slight modification of the procedure by Wernsman, E. A. and D. F. Matzinger [*Hybridization of Crop Plants* W. R. Fehr and H. H. Hadley, eds, pp 657–668 (1980)]. Briefly, flowers from Cre plants were selected on the day before anthesis; the corolla was split longitudinally, the anthers were removed, and the stigma was pollinated with pollen from flowers from loxP plants that were allowed to anthese either on the plant or overnight in a beaker of water. To prevent contaminating pollen from reaching the stigma, a 4 cm length of a cocktail stirrer, one end plugged with modelling clay, was slipped over the stigma and style and held in place by the corolla. Each flower was tagged. Capsules were allowed to grow to maturity and then harvested.

The four loxP plants used in the crosses between heterozygous parents had segregation ratios that suggest the presence of three or more independent loci. All of the Cre plants used had segregation ratios indicating insertion of the cre gene at only one genetic locus. Since both the loxP and Cre parents were heterozygous, the seed produced from hand pollinations of loxP pollen onto the stigmas of emasculated flowers from Cre plants could carry none, both, or either one of the foreign DNA insertions. Therefore, seeds resulting from cross pollinations were screened for the presence of the two marker genes and then assayed for kanamycin resistance: a manifestation of site-specific recombination. To identify only those progeny from cross pollinations that carried both markers 100 to 150 seed from each cross were first screened on chlorsulfuron in a germination assay. Then, shoot cuttings of seedlings resistant to chlorsulfuron were tested for root formation in medium containing hygromycin. Seeds from self-crossed Cre and loxP plants were used as controls at each step. Cre x Cre seed produced only bleached seedlings on chlorsulfuron, indicating herbicide sensitivity. None of the loxP x loxP seedlings rooted on hygromycin.

Selected seedlings that were resistant to both compounds, along with controls, were tested for kanamycin resistance using a callus growth assay. A total of 83 out of 90 seedlings (92%) from 8 crosses involving six different Cre and four different loxP parents, were found to be resistant to kanamycin. Table 5 shows the number of seedlings that were kanamycin resistant for each cross. In six of these crosses all of the plants tested were kanamycin resistant (53/53). Progeny from two crosses yielded about 80% kanamycin resistant progeny (20/24 and 10/13). All of the 63 seedlings tested from self-crosses of the loxP and Cre plants were sensitive to kanamycin.

TABLE 5

Number of Kanamycin Resistant Progeny from Crosses Between Heterozygous Cre and loxP Parents

| FEMALE | | L3[a] | L4 | L5 | L6 |
|---|---|---|---|---|---|
| | self | 0/5 | 0/5 | 0/5 | |
| C1[b] | | 0/9[c] | 13/13 | | |
| C2 | | 0/9 | | 5/5 | |
| C3 | | 0/7 | 2/2 | 4/4 | 16/16 |
| C4 | | 0/9 | | 20/24 | |
| C5 | | 0/5 | 13/13 | | |
| C6 | | | | | 10/13 |

[a] L3–L6 are independent heterozygous loxP transformants used as the pollen parent.
[b] C1–C6 are different heterozygous Cre transformants used as the female parent.
[c] Number of progeny exhibiting kanamycin resistance/number of progeny tested. Resistance was defined as ≥ 0.5 grams callus growth in at least 2 of the 3 leaves tested. Disks were taken from leaves from the distal, middle and proximal portions of the plant to assay for resistance throughout the plant.

Kanamycin resistant plants resulting from genetic crosses of heterozygous loxP plants and Cre plants were assayed by Southern blots to detect recombination. The same NptII fragment probe described in Section D was hybridized to filters containing BamHI digested DNA isolated from progeny of loxP and Cre plants. Of the six progeny DNAs analyzed that were derived from four different crosses involving two loxP plants and four Cre plants, all contained the 5.7 kb fragment and not the 2.4 kb fragment. DNA of progeny that were controls resulting from selfing of loxP plants retain the 2.4 kb fragment demonstrating that Cre is required for recombination. Another probe was used to verify that the DNA located between the two loxP sites was excised in the progeny of crosses. The BamHI-XbaI fragment containing the polyadenylation nucleotide sequence region of a tobacco Rubisco small subunit gene, that is described in Example 5 and diagrammed in FIG. 1C, was labeled and hybridized to the same filters, after washing to remove the first probe. The DNA of progeny of selfed loxP plants contained the 2.4 kb fragment indicating the presence of the polyA sequence while the DNAs of progeny of Cre and loxP plant crosses showed no hybridization to this probe confirming that excision had occurred.

Therefore, both the phenotypic and molecular evidence indicate that Cre mediated site-specific recombination has occurred in these hybrid tobacco seedlings, and the phenotypic data suggests that recombination has occurred in 80% to 100% of the progeny.

G. Site-specific recombination in plant cells following genetic crosses of homozygous loxP and Cre plants A method utilized to produce excisional recombination was to genetically unite the Cre recombinase with the loxP-polyA-loxP DNA fragment, which is integrated in the plant genome, by sexual hybridization of homozygous loxP and Cre plants. Cross pollination using homozygous parents insures the presence of both loxP and cre DNA insertions in all progeny. Plants homozygous for the marker gene linked to loxP-polyA-loxP and plants homozygous for the marker gene linked to cre were identified and utilized to produce site-specific recombination between two loxP sites.

Nine transgenic tobacco plants which had the Hpt marker gene and cre integrated at a single locus, as measured by a 3:1 segregation of the hygromycin resistance in a seed germination assay, were chosen for further crosses. R1 seeds were planted on MX$^-$ medium containing 20–50 mg/l hygromycin to select for plants containing the transferred hygromycin resistance gene. Seedlings which were able to develop on the hygromycin-containing medium were transferred to soil and allowed to grow to maturity in the growth chamber maintained for a 14 hr, 24° C. day, 10 hr, 20° C. night cycle, with approximately 80% relative humidity, under mixed cool white fluorescent and incandescent lights. Bags were placed on individual inflorescences to permit self-fertilization. Seeds (R2) of several plants (R1) derived from individual transformants (R0) were collected and subjected to segregation analysis by plating on MX$^-$ medium containing 50 mg/l hygromycin. R1 plants which were heterozygous would be expected to produce hygromycin resistant progeny with a ratio of 3:1. On the other hand, R1 plants which were homozygous would yield 100% hygromycin resistant progeny after self-fertilization. Using this procedure, homozygous seed stocks of each of the chosen transformants were identified.

Five transgenic tobacco plants which had the resistant ALS marker gene and loxP-polyA-loxP integrated at a single locus, as measured by a 3:1 segregation of chlorsulfuron resistance in a seed germination assay, were chosen for further crosses. R1 seed were planted on MX$^-$ medium containing 100–300 mg/l chlorsulfuron to select for plants containing the transferred chlorsulfuron resistance genes. Seedlings which were able to develop on the chlorsulfuron-containing medium were transferred to soil and allowed to grow to maturity in the growth chamber under conditions described above. As above, bags were placed on individual inflorescences to permit self-fertilization. Seeds (R2) of several plants (R1) derived from individual transformants (R0) were collected and subjected to segregation analysis by plating on MX$^-$ medium containing 300 mg/l chlorsulfuron. R1 plants which were heterozygous would be expected to produce chlorsulfuron resistant progeny with a ratio of 3:1. On the other hand, R1 plants which were homozygous would yield 100% chlorsulfuron resistant progeny after self-fertilization. Using this procedure, homozygous seed stocks of each of the chosen transformants were identified.

Pollen from one homozygous Cre plant, as well as from one WT plant, was used to pollinate three homozygous loxP plants, each derived from an independent primary transformants. To ensure that the hybrid seeds carried both markers, seeds from loxP x Cre crosses were germinated on chlorsulfuron and hygromycin, separately and jointly. All of the germinated seedlings bore true leaves and roots, indicating 100% resistance to both selections. As expected, the progeny of a loxP x WT cross were all chlorsulfuron resistant but hygromycin sensitive.

Figure 3:
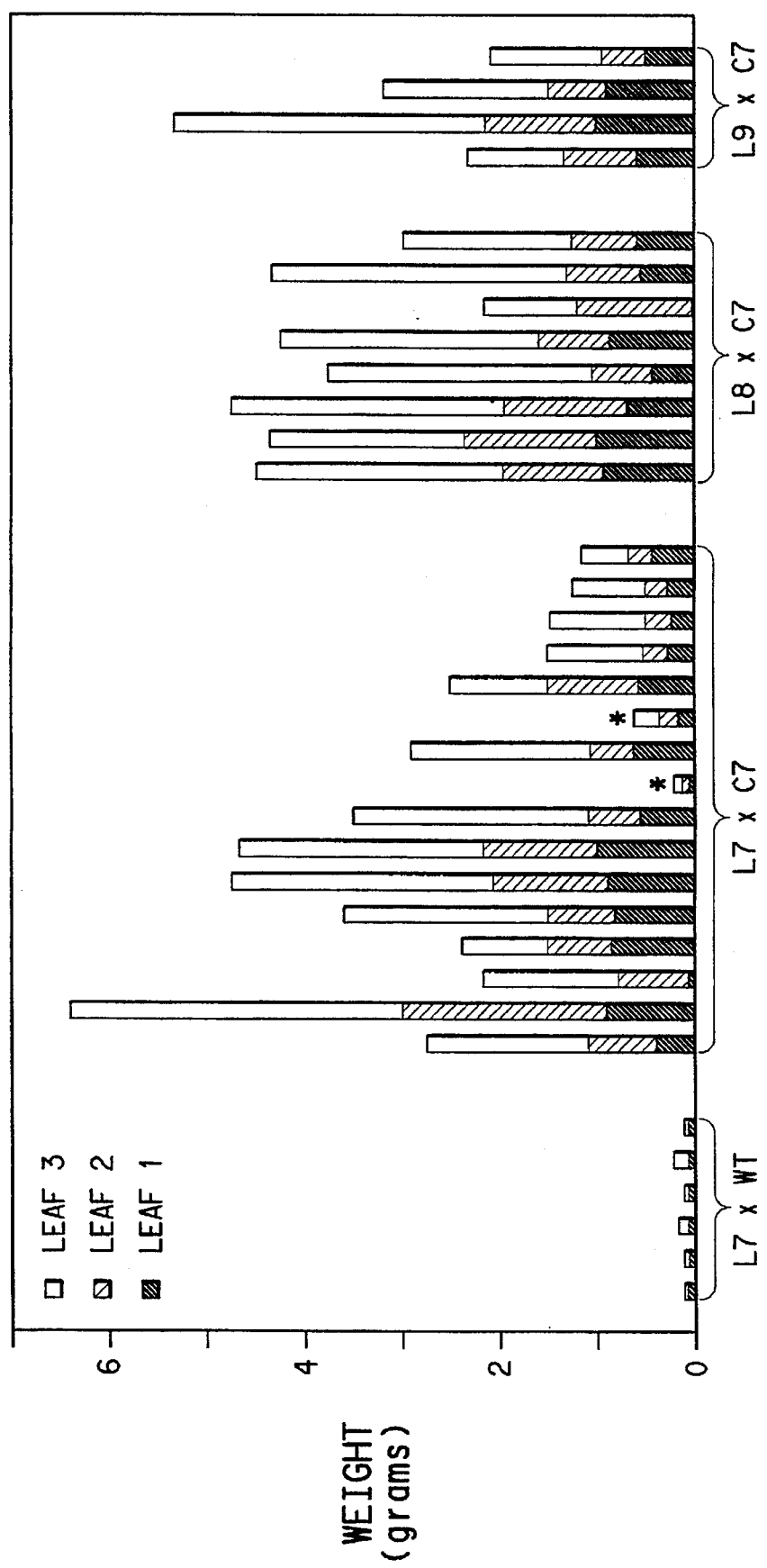
FIG. 3 shows kanamycin resistance in loxP x Cre hybrids from homozygous parents.

Hybrid loxp x Cre seeds from the same stocks tested above were germinated and grown on MX$^-$ medium (Table 2). Tissue from the first through third leaves was tested for growth on kanamycin in a callus induction assay at 25 days after imbibition, and tissue from the fourth through sixth leaves was tested at 40 days after imbibition. The total weight of the leaf disks after three weeks of callus growth is shown in FIG. 3. All seven loxP x WT control progeny tested were sensitive to kanamycin. Most of the 28 progeny from the homozygous loxP x Cre crosses were kanamycin resistant. In two crosses 100% of the progeny were kanamycin resistant in at least 5 of 6 leaves tested (8/8 and 4/4, respectively). Fourteen out of 16 progeny in another cross were resistant to kanamycin in at least four out of six leaves tested. The two plants which appeared to be kanamycin sensitive produced more callus than did the controls, but did not show the extent of callus growth associated with resistance (FIG. 3).

In FIG. 3, C7, L7 and L8 are single locus homozygous plants that were derived from C3, L1 and L2 primary transformants, respectively. L9 is a homozygous loxP plant derived from a primary transformant not used in previous experiments. Each bar represents the weight of 4 leaf disks from an individual offspring, one from each of the first two leaves and two disks from the third leaf, after incubation on callus induction medium (Table 2) for three weeks. About 0.2 grams is contributed by the original leaf disks. The asterisks mark two progeny that exhibit kanamycin sensitivity.

To determine the number of hybrid progeny in which site-specific recombination had occurred, the first, second, and third leaves from 94 seedlings from one cross were tested for kanamycin resistance. Seventy one out of the 94 seedlings were kanamycin resistant in all three leaves tested, indicating that recombination had occurred early in development in 75% of the progeny. However, recombination seems also to have occurred later in development, in that 90% of the seedlings (85/94) exhibited resistance in the third leaf. To assess the incidence of spontaneous kanamycin resistance, 14 self crossed loxP and 13 self crossed Cre seedlings and 16 loxp x WT progeny were tested in a callus induction assay; none were resistant. This reconfirms that the loxP construction is stable through meiosis, even when the plant carrying it is sexually hybridized.

H. Deletion of a sulfonylurea-resistant acetolactate synthase (ALS) marker from transgenic tobacco using the loxP-cre system

EXAMPLE 7

A sulfonylurea (SU) resistance marker gene was eliminated from transgenic tobacco plants, leaving the chimeric 35S/P-GUS (GUS=β-glucuronidase) gene in the genome. A plasmid was constructed containing a SU-resistant ALS gene located between directly oriented loxP sites. The vector pTZ19R (Pharmacia, Inc., Piscataway, N.J.) was digested with HindIII and a synthetic oligonucleotide linker with a nonfunctional HindIII end and XhoI, SalI, HindIII and Asp718 sites was added. This plasmid was digested with HindIII and ligated with the HindIII fragment from pKNKloxA, described in Example 6 that has directly oriented loxP sites on either end, creating pTZlox2. The resulting plasmid was digested with XbaI, this site being located between the loxP sites, and an XbaI fragment containing a chimetic SU-resistant ALS gene was added. This chimeric SU-resistant ALS gene is present as an XbaI fragment in a pTZ vector called pMHP35. It contains the CaMV 35S promoter/Cab22L BglII-NcoI fragment that is described by Harpster et al. [*Mol. Gen. Genet.* 212: 182–190 (1988)]and the Arabidopsis ALS coding and 3' regions, described by Mazur et al. [*Plant Physiol.* 85: 1110–1117 (1987)], that was mutated so that it encodes a SU-resistant form of ALS. The mutations, introduced by site directed mutagenesis, are those present in the tobacco SU-resistant Hra gene described by Lee et al. [*EMBO J.* 5: 1241–1248 (1988)]. The resulting plasmid in which the SU-resistant ALS gene is between loxP sites was named pTZlox2FA. Next the entire lox-ALS-lox fragment was isolated following SalI and Asp718 digestion, and cloned into the binary vector pZS94 that had been digested with the same enzymes creating pZ4loxA.

pZS94 contains the origin of replication and ampicillin resistance gene from pBR322 for maintenance and selection in *E. coli*. It contains the replication and stability regions of the *Pseudomonas aeruginosa* plasmid pVS1, described by Itoh et al. [*Plasmid* 11: 206–220 (1984)], which are required for replication and maintenance of the plasmid in Agrobacterium. Also contained are a T-DNA left border fragment of the octopine Ti plasmid pTiA6 and a right border fragment derived from TiAch5 described by van den Elzen et al. [*Plant Molec. Biol.* 5: 149–154 (1985)]. Between these borders are a LacZ gene and the unique restriction sites HindIII, SalI, BamHI, SmaI, Asp718, and EcoRI derived from pUC18. pZ4loxA was digested with SalI and a SalI fragment containing a chimeric 35S/P-GUS gene was added. This chimeric GUS gene contains the 35S promoter/Cab22L fragment described above, the GUS coding region available from Clonetech, and the Nos 3' region described in Example 1. The resulting plasmid was named pZ4loxAG and is shown in FIG. 4.

Figure 4:
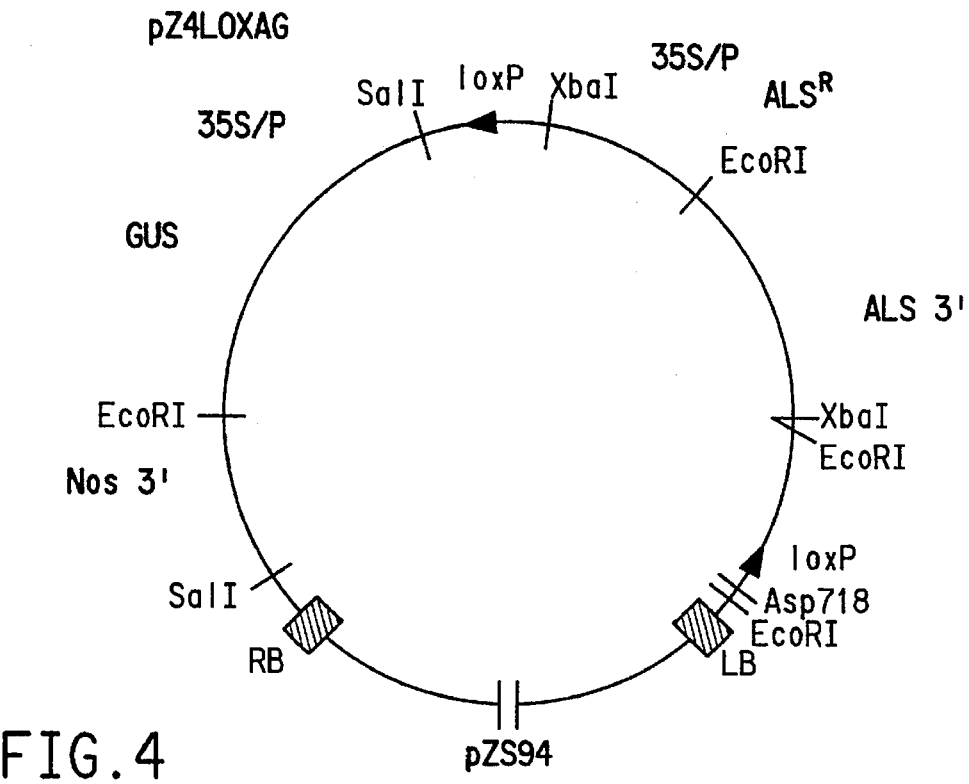
FIG. 4 shows a map of plasmid pZ4LoxAG that was introduced into *Agrobacterium tumefaciens* and then into plants.

In FIG. 4, the pZS94 binary vector contains a chimeric 35S/P-ALS gene that is bounded by directly oriented loop sites, and a chimeric 35S/P-GUS-Nos 3' gene. The loxP sites are indicated by arrowheads.

pZ4loxAG was transferred into *A. tumefaciens* LBA4404 by direct DNA uptake following the procedure described in *Plant Molecular Biology Manual*, [SB Gelvin et al., eds. Kluwer Academic Press PMAN-A3/7, (1988)]. The presence of the binary vector in Agrobacterium colonies selected on mina medium with sucrose (See Table 1) containing 100 μg/ml carbenicillin was verified by restriction digests of miniprep DNA. The resulting Agrobactrium strain was used to obtain tobacco transformants as described in Materials and Methods using resistance to 25 ppb chlorsulfuron for selection of transformants, as detailed below.

Leaf disks were inoculated by submerging them for several minutes in 20 ml of a 1:20 dilution of the overnight culture of Agrobacterium. The culture was started by inoculating 5 ml of YEP medium (Table 8) containing 100 mg/l carbenicillin with a single bacterial colony. The culture was grown for approximately 17–20 hours in a glass culture tube in a New Brunswick platform shaker maintained at 28° C.

After inoculation, the leaf disks were placed in petri dishes containing 0.1N1B agar medium (Table 2) and sealed with parafilm. The petri dishes were incubated under mixed fluorescent and "Gro and Sho" plant lights (General Electric) for 2–3 days in a culture room maintained at approximately 25° C.

To rid the leaf disks of Aqrobacterium and to select for the growth of transformed tobacco cells, the leaf disks were transferred to fresh 0.1N1B medium containing 500 mg/l cefotaxime and 25 ppb chlorsulfuron. Cefotaxime is kept as a frozen 200 mg/ml stock solution and added aseptically (filter sterilized through a 0.45 μm filter) to the media after autoclaving. A frozen chlorsulfuron stock was prepared by first making a 0.2 mg/ml solution in 0.01N NH$_4$OH, which was then diluted 1: 10 with deionized water, and filter sterilized into the autoclaved media. Leaf disks were incubated under the growth condition described above for 18 days and then transferred to fresh media of the same composition.

Fifteen days later, shoots developing on medium containing 25 ppb chlorsulfuron were excised with a sterile scalpel and planted in MX⁻ medium containing 500 mg/l cefotaxime and 25 ppb chlorsulfuron. Root formation was recorded within 2 weeks.

Integration of an intact GUS/loxP/Hra DNA sequence in the plant genome was verified by a callus induction assay for chlorsulfuron resistance and a GUS enzyme activity assay. A leaf piece, approximately 0.2 cm$^2$ in size, was removed from each of several selected rooted excised shoots to test for GUS activity. Presence of GUS activity was determined by grinding each leaf piece in a solution (Table 6) containing 1 mg/ml X-Gluc (5-bromo-4-chloro-3-indolyl-β-gulcuronide) and incubating the tissues 1–16 hours at 37° C. The formation of a blue precipitate indicated the presence of GUS activity.

TABLE 6

Solution for X-Gluc

| Stocks | Volume (ml) |
| --- | --- |
| 0.2 M NaPO$_4$ buffer, pH 7.0 (0.2 M Na$_2$HPO$_4$: 62 ml 0.2 M NaH$_2$PO$_4$: 38 ml) | 25.0 |
| Deionized water | 24.0 |
| 0.1 M K$_3$[Fe(CN)$_6$] | 0.25 |
| 0.1 M K$_4$[Fe(CN)$_6$]·3H$_2$O | 0.25 |
| 1.0 M Na$_2$EDTA | 0.50 |

Leaves from five selected plants exhibiting GUS activity were removed from the rooted excised shoots to determine levels of resistance to chlorsulfuron in a callus induction assay on selective media. To induce callus formation, leaves were excised and 10 leaf disks, 8 mm in diameter, were made using a sterile paper punch and were plated on callus induction medium containing 25 ppb chlorsulfuron and 250 μg/l cefotaxime. Wild-type was used as a control. Leaf disks and the associated callus was weighed; all five transformants exhibited resistance to chlorsulfuron as shown in Table 7.

To test for excision of the ALS marker gene, the five chlorsulfuron-resistant independent transformants that exhibited GUS activity were re-transformed to introduce the cre gene as follows. Healthy leaves were harvested from these five transgenic tobacco plants and a wild-type plant growing in Magenta GA7 vessels (Magenta Corp., Chicago, Ill., USA). Leaf disks were prepared from these axenic leaves using a sterile paper punch, inoculated with Aqrobacterium harboring either the –/Hpt or the Cre/Hpt-B plasmid (Example 4), incubated for three days on 0.1N1B, placed on 0.1N1B medium containing 500 mg/l cefotaxime and 30 mg/l hygromycin, and incubated 2 weeks. Leaf disks were then transferred to fresh medium of the same composition for two weeks, then transferred to FiX- medium containing 500 mg/l cefotaxime and 30 mg/l hygromycin for shoot formation. As shoots appeared, they were excised from the leaf disk and placed in MX⁻ medium containing 500 mg/l cefotaxime and 30 mg/l hygromycin. Shoots were taken from different leaf disks to ensure that they result from independent transformation events. Shoots which rooted were assayed for GUS activity using X-Gluc as described above. Sixty-three shoots tested had GUS enzyme activity while three did not exhibit GUS activity. The parent pZ41oxAG plant of these three retransformants appears to be chimeric for GUS expression.

Leaf disks were taken from each plant and tested in a callus induction assay as described above. Results are shown in Table 7. Ninety-one percent of all plants resulting from re-transformation with –/Hpt remained chlorsulfuron resistant, as expected, since the Cre recombinase was not introduced. Ninety-five percent of the plants resulting from re-transformation of pZ4LoxAG plants with Cre/Hpt-B exhibited sensitivity to chlorsulfuron; only two out of 38 plants remained resistant to chlorsulfuron. These data indicate that the sulfonylurea-resistant ALS gene is no longer functioning in a majority of those plants which received the cre coding region, suggesting that it has been excised by cre-mediated recombination at loxP sites.

To verify that excision has occurred, DNA prepared from re-transformants was analyzed on Southern blots. The DNA was digested with EcoRI before gel electro-phoresis and transferred to filters. A DNA fragment consisting of the 35S promoter was prepared, radioactively labeled, and hybridized to the blotted plant DNA. A 6 kb band was detected in re-transformants that did not receive cre. This band represents a DNA fragment extending from an EcoRI site located 3' to the GUS coding region to an EcoRI site located within the ALS coding region (see FIG. 4). It includes the GUS coding region, the 35S promoter that regulates expression of GUS, the 35S promoter that regulates expression of ALS and a portion of the ALS coding region. A 3.2 kb band was detected in DNA from plants that received cre. This band represents a DNA fragment extending from the EcoRI site located 3' to the GUS coding region to an EcoRI site located just outside of the distal loxP site. It includes the GUS coding region and the 35S promoter regulating GUS expression. The shift of the detected fragment size from 6 kb to 3.2 kb verifies the excision of the DNA segment located between the loxP sites, including the ALS coding region and the 35S promoter that regulates its expression.

TABLE 7

Number of Chlorsulfuron Resistant and Sensitivel Plants Recovered after Re-transformation with -/Hpt and Cre/Hpt-B as Determined by a Callus Induction Assay

| Original | | Re-transformed | | |
| --- | --- | --- | --- | --- |
| | | Htp/- | | Cre/Hpt-B |
| Transformant | | # | # | # | # |
| ID | Resistant? | Resistant | Sensitive | Resistant | Sensitive |
| D1 | yes | 7 | 0 | 2 | 11 |
| D2 | yes | 4 | 0 | 0 | 5 |
| D3 | yes | 9 | 0 | 0 | 8 |
| D4 | yes | 6 | 0 | 0 | 8 |
| D5 | yes | 4$^2$ | 2 | 0 | 4 |
| WT | no | 0 | 1 | | |

[1]Resistant is defined as average weight per leaf disk ≥ 1.0 gram and sensitive is defined as average weight per leaf disk ≤ 0.2 grams.
[2]One of these transformants was resistant in one experiment and sensitive in another experiment.

EXAMPLE 8

Deletion of a SU-resistant ALS marker gene from transgenic arabidopsis using the loxP-cre system A sulfonylurea (SU) resistance marker gene was eliminated from transgenic Arabidopsis plants, leaving the chimetic 35S/P-GUS gene in the genome. Plasmid construction and transformation of Agrobacterium are described in Example 7.

Standard aseptic techniques for the manipulation of sterile media and axenic plant/bacterial cultures are followed, including the use of a laminar flow hood for all transfers. Compositions of the culture media are listed in Table 8.

Unless otherwise indicated, 25×100 mm petri plates, sealed with filter tape (Carolina Biological Supply Co., Burlington, N.C.), were used for plant tissue cultures. Incubation of plant tissue cultures was at 23° C. under constant illumination with mixed fluorescent and "Gro and Sho" plant lights (General Electric) unless otherwise noted.

The source of explants was in vitro grown roots of *Arabidopsis thaliana* (L.) Heynh, geographic race Wassilewshija. Seeds were sterilized for 10 min in a solution of 50% commercial bleach with 0.1% SDS, rinsed three to five times with sterile water, dried thoroughly on sterile filter paper, and then 2–3 seeds were sown in 50 ml liquid Gamborg's B5 medium (Gibco #560-1153) in 250 ml Belco flasks. The flasks were capped, placed on a rotary shaker at 70–80 rpm, and incubated for 3–4 weeks.

Prior to inoculation with Agrobacterium, root tissues were cultured on callus induction medium (MSKig, infra). Roots were harvested by removing the root mass from the Belco flask, placing it in a petri dish, and using forceps, pulling small bundles of roots from the root mass and placing them on MSKig medium. Petri dishes were sealed with filter tape and incubated for four days.

Cultures of Agrobacterium cells containing the binary plasmid pZ4loxAG, as previously described, were grown in 5 ml of YEP medium containing 100 mg/l carbenicillin. Cultures of Agrobacterium cells containing the binary plasmid Cre/Hpt-B (Example 3) were grown in 5 ml of YEP medium containing 5 mg/l tetracycline. The cultures were grown for approximately 17–20 hours in glass culture tubes in a New Brunswick platform shaker (225 rpm) maintained at 28° C. Pre-cultured roots were cut into 0.5 cm segments and placed in a 100 μm filter, made from a Tri-Pour beaker (VWR Scientific, San Francisco, Calif. USA) and wire mesh, which is set in a petri dish. Root segments were inoculated for several minutes in 30–50 ml of a 1: 20 dilution of the overnight Agrobacterium culture with periodic gentle mixing. Inoculated roots were transferred to sterile filter paper to draw off most of the liquid. Small bundles of roots, consisting of several root segments, were placed on MSKig medium containing 100 μM Acetosyringone (3',5'-Dimethoxy-4'-hydroxyaceto-phenone, Aldrich Chemical Co., Milwaukee, Wis., USA). Petri plates were sealed with parafilm or filter tape and incubated for two to three days.

After infection, root segments were rinsed and transferred to shoot induction medium with antibiotics as detailed below. Root bundles were placed in a 100-μm filter unit (described above) and rinsed with 30–50 ml liquid MSKig medium. The filter was vigorously shaken in the solution to help remove the Agrobacterium, transferred to a clean petri dish, and rinsed again. Roots were blotted on sterile filter paper and bundles of roots were placed on MSg (infra) medium containing 500 mg/l vancomycin and either 25 ppb chlorsulfuron (pZ4loxAG) or 15 mg/l hygromycin (Cre/Hpt and –/Hpt). Plates were sealed with filter tape and incubated for 12 to 14 days.

Green nodules and small shoot primordia were visible at about 2–3 weeks. The explants were either left intact or were broken into numerous pieces and placed on GM medium containing 200–300 mg/l vancomycin and either 25 ppb chlorsulfuron (pZ4loxAG) or 10 mg/l hygromycin (Cre/Hpt and –/Hpt) for further shoot development. Plates were either sealed with two pieces of tape or with filter tape. As they developed, individual shoots were isolated from the callus and were placed on MSRg medium containing 100 mg/l vancomycin and either 25 ppb chlorsulfuron (pZ4loxAG) or 10 mg/l hygromycin (Cre/Hpt and –/Hpt). Dishes were sealed as described above and incubated for seven to 10 days. Shoots were then transferred to GM medium containing 100–200 mg/l vancomycin in 25×100 petri dishes or Magenta G7 vessels. Many primary transformants (T1) which were transferred to individual containers set seed (T2).

T2 seed was harvested from selected putative transformants and sown on GM medium containing either 25 ppb chlorsulfuron (pZ4loxAG) or 10–30 mg/l hygromycin (Cre/Hpt and –/Hpt). Plates were cold treated for 2 or more days at 4° C., and then incubated for 10 to 20 days at 23° C. under constant illumination as described above. Seedlings were scored as resistant (green, true leaves develop) and sensitive (no true leaves develop).

Selected chlorsulfuron or hygromycin resistant T2 seedlings were transplanted to soil and were grown to maturity at 23° C. daytime (14 hours), 18° C. nighttime (10 hours), at 65–80% relative humidity.

Genetic crosses of Cre/Hpt-B plants (hygromycin resistant) and pZ4loxAG plants (chlorsulfuron resistant) were performed and the resulting seed allowed to mature. Seed was collected, sterilized, plated on GM (Table 8) containing 30 mg/l hygromycin, and tissue from the seedlings tested for GUS activity with X-gluc as previously described. Those seedlings exhibiting both hygromycin resistance and GUS activity (indicating that they received both the cre gene and the loxP construction), were allowed to grow until stem tissue could be obtained for a callus induction assay. Stem tissues were obtained from selected transformants and placed on MSKig medium with and without 25 mg/l chlorsulfuron. Callus growth was recorded within three weeks. pZ4LoxAG plants were allowed to self-pollinate, seed was collected, sterilized, plated on GM containing 25 ppb chlorsulfuron, and used as controls (see Table 9 for results). Sensitivity to chlorsulfuron in the majority of GUS positive seedlings resulting from crosses between Cre/Hpt-B and pZ4LoxAG plants indicates that in these seedlings, the SU-resistant ALS marker gene was no longer functioning, suggesting it has been excised by Cre-mediated recombination between loxP sites.

Chlorsulfuron sensitive plants were placed in soil and are allowed to mature. T3 seed is collected, sterilized, and germinated on GM medium with or without 30 mg/l hygromycin or 25–100 ppb chlorsulfuron. Plates are sealed with filter tape, cold treated for 2 or more days at 4° C., and then incubated for 10 to 20 days at 23° C. under constant illumination as described above. Seedlings are scored as resistant and sensitive and the results recorded. Representative seedlings are screened for GUS activity. Some seedlings exhibit GUS activity, but are not resistant to chlorsulfuron indicating that the SU-resistant ALS marker gene is no longer functioning, suggesting that it has been excised by Cre-mediated recombination between loxP sites.

To verify that excision has occurred, DNA prepared from these plants is analyzed on Southern blots. The DNA is digested with EcoRI before gel electrophoresis and transferred to filters. A DNA fragment consisting of the 35S promoter is prepared, radioactively labeled, and hybridized to the blotted plant DNA. A 6 kb band is detected in re-transformants that did not receive cre. This band represents a DNA fragment extending from an EcoRI site located 3' to the GUS coding region to an EcoRI site located within the ALS coding region (see FIG. 4). It includes the GUS coding region, the 35S promoter that regulates expression of GUS, the 35S promoter that regulates expression of ALS, and a portion of the ALS coding region. A 3.2 kb band is detected in DNA from plants that received cre. This band represents a DNA fragment extending from the EcoRI site located 3' to the GUS coding region to an EcoRI site located just outside of the distal loxP site. It includes the GUS coding region and the 35S promoter regulating GUS expression. The shift of the detected fragment size from 6 kb to 3.2 kb verifies the excision of DNA segment located between the loxP sites, including the ALS coding region and the 35S promoter that regulates its expression.

TABLE 8

Medium Composition

| YEP MEDIUM | Per Liter |
|---|---|
| Bacto Peptone | 10.0 g |
| Bacto Yeast Extract | 10.0 g |
| NaCl | 5.0 g |
| Agar (optional) | 15.0 g |
| pH 7.0 | |
| BASIC MEDIUM | |
| 1 pkg. Murashige and Skoog Minimal Organics Medium without Sucrose (Gibco #510 or Sigma # M6899) | |
| 10 ml Vitamin Supplement | |
| 0.05% MES | 0.5 g/l |
| 0.8% agar | 8 g/l |
| pH 5.8 | |
| VITAMIN SUPPLEMENT - 100 × Stock | |
| 10 mg/l thiamine | |
| 50 mg/l pyridoxine | |
| 50 mg/l nicotinic acid | |
| GM = Germination Medium | |
| Basic Medium | |
| 1% sucrose | 10 g/l |
| MSKig = Callus Induction Medium | |
| Basic Medium | |
| 2% glucose | 20 g/l |
| 0.5 mg/l 2,4-D | 2.3 µM |
| 0.3 mg/l Kinetin | 1.4 µM |
| 5 mg/l IAA | 28.5 µM |
| MSg = Shoot Induction Medium | |
| Basic Medium | |
| 2% glucose | 20 g/l |
| 0.15 mg/l Indole-3-Acetic Acid (IAA) | 0.86 µM |
| 5.0 mg/l N$^6$-($\Delta_2$ Isopentenyl)-Adenine 2iP | 24.6 µM |
| MSRg = Shoot Induction Medium | |
| Basic medium | |
| 2% glucose | 20 g/l |
| 12 mg/l Indole-3 Butyric Acid (IBA) | 58.8 µM |
| 0.1 mg/l Kinetin | 0.46 µM |

TABLE 9

Results of Assays of Seedlings Resulting from Crosses between pZ4loxAG and Cre/Hpt-B Arabidopsis Plants

| Female | Male | # Chlorsulfuron Sensitive Seedlings/ # GUS Positive, Hygromycin Resistant Seedlings Tested |
|---|---|---|
| E1 | B6 | 42/42 |
| E2 | B4 | 0/5 |
| E3 | B3 | 4/4 |
| E4 | B5 | 7/7 |
| E5 | B3 | 1/1 |

EXAMPLE 9

Expression of Cre from the chemically regulated corn promoter In2-2

Cre expression was placed under control of the In2-2 promoter, that is induced by N-(aminocarbonyl)-2-chlorobenzenesulfonamide, by constructing the chimeric gene: In2-2/P-cre-Nos 3'. The starting material for the construction was the plasmid Cre/Hpt-A, which was described in Examples 1 and 2. Cre/Hpt-A was digested with HindIII and SalI and the DNA fragment containing the cre coding region and the Nos 3' was isolated. This HindIII-SalI fragment was subcloned into the vector Bluescript SK(+) (Stratagene, catalog 212205) that had been digested with HindIII and SalI and dephosphorylated, yielding the plasmid designated pBSCre.

The addition of the In2-2 promoter to pBSCre was accomplished using plasmids HPH 463 dam(−) and 2-2(3.9) which have been described in WO 90/11361. The plasmid 2-2(3.9) is a pUC18 plasmid containing a 3.9 kb SalI fragment derived from the genomic clone containing the 2-2 gene. The 3.9 kb fragment includes 3.6 kb of promoter sequence located 5' of the translation start site and 180 bp of the coding region for the 2-2 protein. The plasmid pHPH 463 dam(−) is a Bluescript S/K(+) plasmid containing a chimeric promoter that has 136 bp of 2-2 promoter Joined to the 5' untranslated leader from the maize alcohol dehydrogenase (ADH) 1-1S allele [Dennis et al., Nucl. Acids Res. 12: 3983–4000 (1984)], with an NcoI site incorporated at the translation start codon. HPH 463 dam(−) was digested with ClaI and the resulting 5' overhangs were filled in with Klenow. The resulting DNA was then digested with XbaI and the ClaI blunt-XbaI fragment containing the 3' part of the 2-2 promoter and maize ADH leader was isolated. The plasmid pBSCre was digested with HindIII and the resulting 5' overhangs were rendered blunt with Klenow. This pBSCre DNA was then digested to completion with XbaI (located in the polylinker) and dephosphorylated using calf intestinal phosphatase. The ClaI blunt-Xba I fragment derived from HPH46dam(−) and the dephosphorylated pBSCre vector were then ligated together to yield the plasmid designated pBSCre101. This construction contains a cre coding region under the transcriptional control of a modified 2-2 promoter that includes a 5' untranslated leader sequence from the maize ADH gene.

Next the 5' distal portion of the In 2-2 promoter was added to pBSCre101. The plasmid 2-2(3.9), described above, was digested to completion with XbaI and AatII and a fragment containing 1.2 kb of the 2-2 promoter was isolated. The plasmid pBSCre101 was digested with XbaI and AatII, dephosphorylated and ligated to the XbaI-AatII fragment from 2-2(3.9). The resulting construction was designated pBSCre102.

Figure 5:
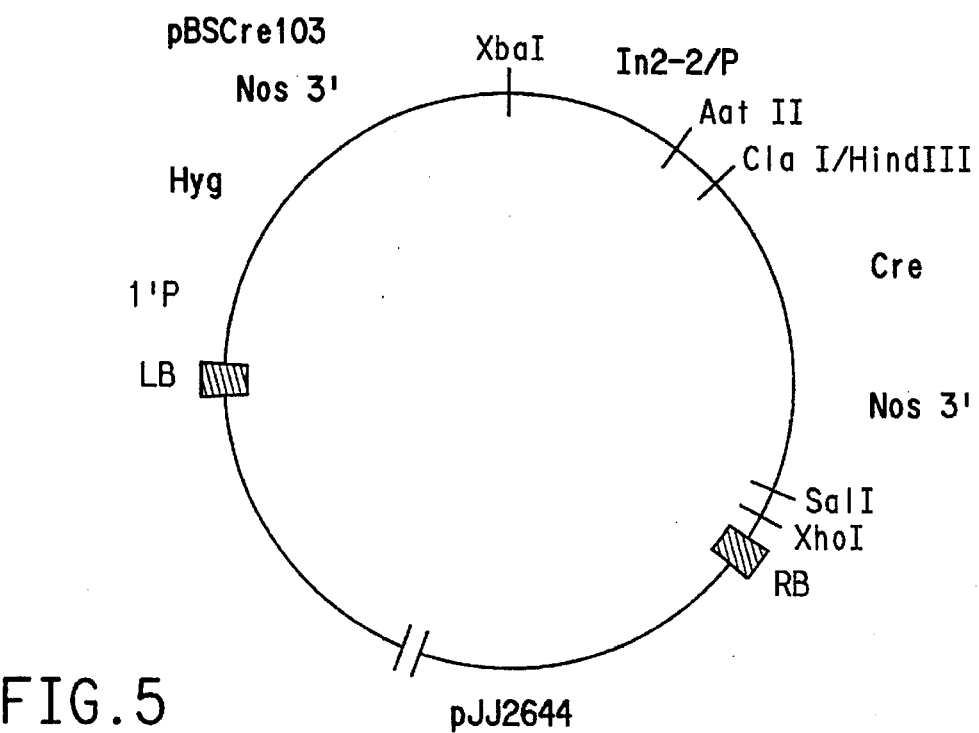
FIG. 5 shows a map of plasmid pBSCre103 that was introduced into *Agrobacterium tumefaciens* and then into plants.

Next pBSCre102 was digested with XbaI and XhoI and the fragment containing the entire In2-2/P-cre-Nos 3' chimeric gene was ligated to pJJ2644 that had been digested with XbaI and XhoI and dephosphorylated, resulting in pBS103. pJJ2644 was described in Example 4. pBSCre103, shown in FIG. 5, was transformed into A. tumefaciens and the resulting strain used to obtain tobacco transformants as described in Materials and Methods; 30 mg/l hygromycin was used for selection and leaf disks were placed on fresh medium every two to three weeks.

Independent primary transformants were grown in magenta boxes, and young leaves were harvested and frozen in liquid nitrogen. One week after the initial harvest, shoot tips were harvested and placed in 15-ml Falcon tubes filled with 0.5× Hoagland's solution (Table 11) containing 200 mg/l N-(aminocarbonyl)-2-chlorobenzenesulfonamide. The plants were allowed to take up inducer for approximately 24 hours. The induced shoots were then harvested, frozen in liquid nitrogen and stored at −80° C.

Total RNA was isolated from both sets of samples as described by Colbert et al. [*Proc. Natl. Acad. Sci. USA* 80: 2248–2252 (1983)]. Replicate RNA samples from both uninduced and induced transformed plants were transferred to nitrocellulose filters and probed with nick translated pBSCre. Twenty-six primary transformants had little to no cre mRNA in the uninduced state, and a strongly hybridizing cre mRNA signal after treatment with N-(aminocarbonyl)-2-chlorobenzene-sulfonamide. This result demonstrates that expression of the cre gene was successfully regulated when under control of the In2-2 promoter.

TABLE 10

0.5× Hoagland's Nutrient Solution 1.0 mM ammonium phosphate, monobasic
4.0 mM potassium nitrate
4.0 mM calcium nitrate
2.0 mM magnesium sulfate
1.0 mM ammonium nitrate
5.0 ppb Sequestrene
9.2 µM manganese chloride
46.0 µM boric acid
0.77 µM zinc sulfate
0.32 µM cupric sulfate
0.11 µM molybdic acid

EXAMPLE 10

Chemical regulation of loxP-cre mediated recombination

Transformants containing the In2-2/P-cre-Nos 3' gene that respond to induction by N-(aminocarbonyl)-2-chlorobenzenesulfonamide, described in Example 9, were crossed, as described in Section F, with the homozygous loxP plants that were described in Section G. The resulting seed is germinated on hygromycin to select those progeny that receive the cre gene. All progeny receive the loxP construction from the homozygous parent. Leaf disks are taken from selected progeny and induced to callus on kanamycin medium as described previously. Lack of callus formation indicates that the lox construction, in which the kanamycin resistance gene is nonfunctional due to the loxP-polyA-loxP fragment insertion, remains intact and that no recombination has occurred. Cre expression is also induced in progeny by treating with N-(aminocarbonyl)-2-chlorobenzene-sulfonamide or related inducing chemicals by spraying, by cutting off the shoot tip or a leaf and allowing uptake through the vascular system, or by placing tissue explants on inducer-containing medium. Following induction, leaf disks are again assayed for callus growth on kanamycin. Growth of this tissue indicates that Cre-mediated recombination at the loxP sites excises the polyA fragment and restores function of the kanamycin resistance gene. Thus recombination occurs only after the inducing chemical is applied to plants containing the In2-2/P-cre-Nos 3' gene and a loxP construction.

EXAMPLE 11

Restoration of fertility in a molecular genetic approach to hybrid seed production An anther promoter-cell disruption chimeric gene (A/P-CD) causing male sterility is deleted from the genome of the hybrid plant resulting in fertility restoration. The A/P-CD gene used consists of the TA29 promoter, the barnase coding region, and the NOS 3' end as described in EPA 89-344029. A binary vector is constructed to consist of the A/P-CD gene flanked by directly repeated loxP sites, and a chimeric NptII gene as a kanamycin resistance selection marker, between the left and right T-DNA border sequences. A diagram of the T-DNA of the binary vector is shown below:

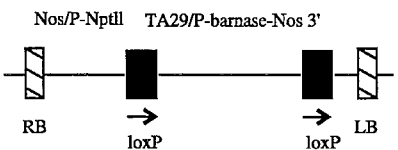

This plasmid, called Lox/AD, is transferred into *A. tumefaciens* LBA4404 and the resulting strain is used to obtain tobacco transformants as described previously. The resulting transformants containing Lox/AD are grown to maturity and tested for male sterility, which indicates correct expression of the A/P-CD gene. Male sterile Lox/AD plants are identified as those that produce no seed upon selfing and/or produce no pollen. These plants are fertilized with pollen from homozygous 35S/P-Cre plants, obtained in Section C, and seed is harvested as previously described. Seeds are sterilized and planted on MX− medium in the presence of kanamycin. Seedlings which are resistant to kanamycin, and therefore have received the Lox/AD construction, are grown to maturity and tested for male fertility. Restoration of fertility is identified by the ability to develop pollen and produce seed upon selfing. Fertility restoration indicates that the A/P-CD gene is deleted due to interaction of Cre protein with the loxP sites.

EXAMPLE 12

Cre-lox mediated disruption of F1 seed development

F1 seed development is aborted by activating a seed disruption gene using the loxP-Cre system. One component of a seed disruption gene is a promoter that is only expressed in the seed. This type of promoter can be derived from a gene whose expression is naturally associated with the embryo and/or endosperm. Desirable promoters to use are derived from the embryo-expressed β-subunit of phaseolin (β-Ph), or from the a subunit of β-conglycinin of soybean (a'-β-CG), which is highly expressed early in seed development in the endosperm and embryo. These two genes are described by Doyle et al. [*J. Biol. Chem.*, 261: 9228–9238 (1986)].

A second component of the seed disruption gene is a coding region which produces a protein that disrupts normal cell functions. An example is the coding region for barnase derived from *Bacillus amyloliquefaciens*, which has been cloned and characterized by Hartley [*J. Mol. Biol.* 202: 913–915 (1988)]and used in EPA 89-344029. The third component is a polyadenylation signal sequence region, which can be derived from the 3' end of most any gene that is functional in plant cells. In this example we use the 3' region from the bean phaseolin gene [Chee et al., *Gene* 41: 457 (1986)]. The seed disruption gene is made into an inactive form by placing a loxP-poly-A-loxPDNA fragment between the promoter and coding region as described for the NOS/P-NptII gene in Example 5. Inactive and active (control) chimeric genes containing either the D-Ph or the a'-β-CG promoter, the barnase coding region (bar), and the phaseolin 3' region (Ph 3') are constructed as follows.

Plasmids containing the β-Ph promoter and Ph 3' or the a'-β-CG promoter and Ph 3' called pUC18pvPpvS and pUC18gmPpvS, respectively, were obtained from Dr. Jerry Slightom, the Upjohn Company. The promoter and 3' regions contained in these two plasmids were synthesized from the genes described by Doyle et al. [*J. Biol. Chem.*, 261: 9228–9238 (1986)] using the polymerase chain reaction (PCR) procedure described by Saiki et al. [Science, 239: 487–491 (1987)]. During the PCR procedure an NcoI site was added at the translation start ATG and 5' to the Ph 3' sequence by incorporating the NcoI restriction site recognition sequence into the appropriate synthetic oligonucleotide primers. A HindIII site was similarly added at the 5' end of the promoter fragments. The synthetic promoter and 3' region fragments were joined at the introduced NcoI sites and ligated into the HindIII site of pUC18 (a HindIII site occurs naturally at the end of the Ph 3' fragment). The resulting plasmids, pUC18pvPpvS and pUC18gmPpvS, were each digested with EcoRI and SalI, the ends filled in using the Klenow enzyme, and religated to delete the polylinker sites located between EcoRI and SalI. The resulting plasmids were named CW104 and CW105, respectively. Each of these plasmids was then digested with NcoI and a synthetic oligonucleotide with restriction sites: NcoI, SmaI, KpnI, XbaI, and incomplete NcoI was added. The resulting plasmids were named CW108 and CW109.

Since the barnase enzyme is lethal to cells, an inhibitor of barnase called barstar is expressed in the Same cells. The pMT420 plasmid containing the barstar and barnase genes isolated from *Bacillus amyloliquefaciens* was obtained from Dr. Robert Hartley, NIH. These genes are described by Hartley [*J. Mol. Biol.* 202: 913–915 (1988)]. The barstar gene was isolated from pMT420 as a PstI-HindIII fragment and ligated into PstI (a unique PstI polylinker site is located after the HindIII site at the 3' end of the Ph 3' fragment) and HindIII digested CW108. A plasmid that retains the HindIII β-Ph promoter and Ph 3' fragment and contains the barstar gene was identified and named 108B. The NcoI-PstI fragment containing Ph 3' and barstar was isolated and ligated to NcoI and PstI digested CW109 creating 109B.

The complete barnase protein includes a pre-sequence involved in secretion, a pro-sequence involved in folding, and the mature protein sequence containing the enzyme activity. We propose that expression of only the mature protein is most effective in disrupting plant cells. Though EPA 89-344029 makes use of barnase as a plant cell disruption protein, it does not disclose details on construction of a barnase gene for expression in plant cells. No information is given on the portion of the barnase coding region that is expressed.

To prepare a DNA fragment containing the coding region for the mature barnase protein (bar), *Bacillus amyloliquefaciens* DNA was used as a template for the PCR procedure described by Saiki et al. [*Science* 239: 487–491 (1987)]. Synthetic primers were made that add an NcoI site, including an in-frame translation start ATG, at the 5' end of the mature protein coding region and an XbaI site following the translation stop codon. The amplified DNA fragment was digested with NcoI and XbaI and ligated to NcoI and XbaI digested 108B creating 108BB, which then contains an active form of the seed disruption gene. Similarly, 109BB is constructed.

To prepare inactive forms of the seed disruption gene, first the NcoI site at the 3' end of the promoter fragment was removed from CW108 and CW109, described above, by digesting each plasmid with NcoI and treating with S1 nuclease. S1 treated CW108 was religated, a plasmid missing the NcoI site was identified by restriction mapping and DNA sequencing, and named 108N. S1 treated CW109 was digested with SmaI (the site is adjacent to the NcoI site) and religated. A plasmid missing the NcoI site was identified by restriction mapping and DNA sequencing and named 109N1. 109N1 was digested with Asp718 and XbaI and a synthetic oligonucleotide linker with the sites Asp718, XhoI, NcoI, and XbaI was added. The resulting plasmid named 109N1X was digested with XhoI and NcoI and an XhoI-NcoI loxP-polyA-loxP DNA fragment was added. This fragment was prepared from p69ssN, a derivative of pBS69polyA, which was described in Example 5. To make p69ssN, pBS69polyA was digested at the HindIII site located outside of one loxP site, the ends filled in, and NcoI linkers were added. 109N1X containing the loxP-polyA-loxP fragment was called 109lox2. This plasmid is digested with NcoI and PstI and the NcoI-PstI fragment prepared from 109BB containing bar, Ph 3', and barstar is added creating 109lox2BB. This plasmid contains an inactive seed disruption gene. 108N is digested with Asp718 and PstI and the Asp718-PstI fragment prepared from 109ssl ox2BB is added. The resulting plasmid is named 108lox2BB and contains an inactive seed disruption gene.

The inactive and active cell disruption genes are each moved into a binary vector with an NptII gene within the borders and a barstar gene added outside of the T-DNA borders. The resulting plasmids are called pZ108lox2BB, pZ109lox2BB, pZ108BB, and pZ109BB. These plasmids are transferred into a disarmed *A. tumefaciens* and the resulting strains are used to obtain transformants as previously described.

Expression of the cre coding region is more effective either with the same developmentally controlled promoter or with the highly active 35S promoter. The cre coding region was placed under control of the same seed promoters used for the disruption genes making chimeric SP-cre-Ph 3' genes: 108Cre and 109Cre. These genes were cloned into binary vectors between the T-DNA borders along with a chimeric sulfonylurea resistance selection marker gene, creating pZ108Cre and pZ109Cre plasmids. These plasmids are transferred into a disarmed *A. tumefaciens* and the resulting strains are used to obtain tobacco or Arabidopsis transformants as previously described. Homozygous single locus plants are derived from primary transformants as previously described.

Homozygous plants transformed with pZ108lox2BB or pZ109lox2BB are crossed with homozygous plants containing pZ108Cre or pZ109Cre, and with the homozygous Cre plants described in Section C or Example 9. Seed pods or siliques are checked for the absence of seed indicating that the seed disruption gene is activated by the loxP-cre system.

EXAMPLE 13

F1 seed development is normal and F2 seed development is aborted by activating a seed maternal tissue disruption gene using the loxP-cre system. A seed maternal tissue disruption gene is made consisting of the mature barnase coding region described above and a promoter region isolated from a seed coat or nucellus-specific gene.

A nucellus-specific gene was isolated and the promoter activity was tested in the transgenic system using the following procedures, Part I. A-F. The cell destructive DNA constructs are made according to the procedures described in Part II.

Seed coat or Nucellus-specific Promoter Isolation

Isolation and Characterization of Maternally Inherited Seed-Specific cDNAs from Watermelon Gene controlling elements that are specific for the maternal tissues in seed are required for this invention of seedless fruit production. To obtain such elements, immature watermelon (*Citrullus vulgaris*, cv. Oasis) fruits were harvested from the Money's Farm in Middle Town, Del., in the late summer, 1990. More than 2000 immature seeds, 2 to 6 mm in length, were collected from these young fruits, and dissected under the microscope. The fleshy white seed coat (containing the outer and inner layers of seed coat and nucellus) and the transparent watery developing embryo sac (containing the embryo and endosperm) were collected separately.

Poly(A)$^+$-RNA was purified from these tissues using total RNA Extraction and mRNA Purification Kits (Pharmacia) according to the manufacturer's specifications, and the developing seed coat/nucellus cDNA library was made by Stratagene. Duplicate filters made from plates of the library, or duplicate dot blots containing DNA made from each individual cDNA clone (rescued from lambda ZAP II clones according to Stratagene's instructions), prepared according to Conkling et al. [Plant Physiology. 93, 1203–1211 (1900)] were differentially screened using $^{32}$P-labeled cDNA probes made from the seed coat/nucellus poly(A)-RNA or from leaf poly(A)-RNA according to Sargent [Guide to Molecular Cloning Techniques, Berger and Kimmel, eds. 423–432 (1987)]. The putative positive clones, which hybridized to the seed coat/nucellus probe and not the leaf probe, were screened three times and characterized by Southern blot, Northern blot, RNA-PCR (Perkin-Elmer Cetus), and in situ hybridization (Cox and Goldberg, 1988, in Plant Molecular Biology: A Practical Approach, C. H. Shaw, ed. Oxford: IRL Press, pp. 1–34) analyses. One clone, WM403, was identified to show predominant if not exclusive expression in the nucellus layer of watermelon seed (WM403 is deposited into ATCC). The watermelon genomic DNA was purified and digested with BamHI, EcoRI, and HindIII restriction enzymes, respectively. The Southern blot analysis was performed using the random primed $^{32}$P-labeled WM403 cDNA as the probe. The result indicates WM403 was encoded by a small gene family (2–3 genes).

Spatial and Developmental Regulation of the Gene Coding for the WM403 Transcript An ideal promoter element for this project is not only specific to seed maternal tissue, but also expressed early enough to assure the completion of the excision/activation event, and the expression of the lethal gene in the target cells. Therefore, the spatial and developmental regulation prior to and post anthesis for the gene encoding WM403 was investigated. The result of Northern blot analysis is shown in FIG. 6.

The female flowers and buds were collected from watermelon plants grown in the walk-in growth chamber (24° C./20° C. for day/night temperature with 14 hr/10 hr photoperiod). According to the ovary size and flowering time, they were grouped into four stages. Stages 1 and 2 are the buds with an ovary length of 0.5–1.0 cm and 1.0–1.5 cm, respectively. Stages 3 and 4 are the flowers at anthesis, and one day post anthesis, respectively. Since the flowers were not bagged, pollination or even fertilization might have occurred in the flowers of stages 3 or 4. The buds or flowers were dissected into two parts: one part contained the intact ovary ($O_1$–$O_4$ were the ovaries harvested from stages 1 to 4 female flowers), and the other part contained the remaining female floral tissues including the stigma, style, petals and sepals ($T_1$–$T_4$ were the tissues harvested with the corresponding ovaries of stages 1 to 4 female flowers). Leaves, roots, and immature male flower buds were also collected for analysis. Total RNAs were extracted from these tissues, agarose gel electrophoresed, membrane blotted, and hybridized to the $^{32}$P-labeled cDNA insert of WM403.

Figure 6A:
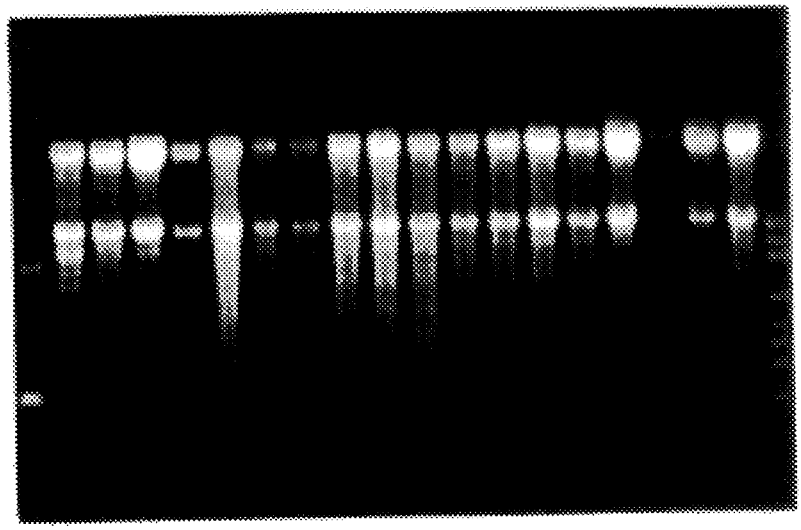
FIGS. 6A, 6B and 6C show a Northern blot analysis of the differential gene expression of WM403 in various watermelon tissues.
Figure 6B:
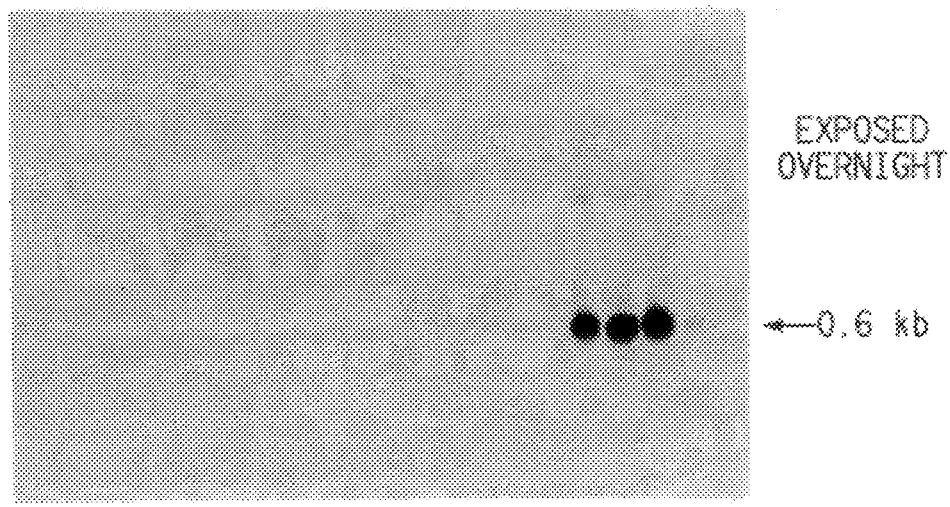
Figure 6C:
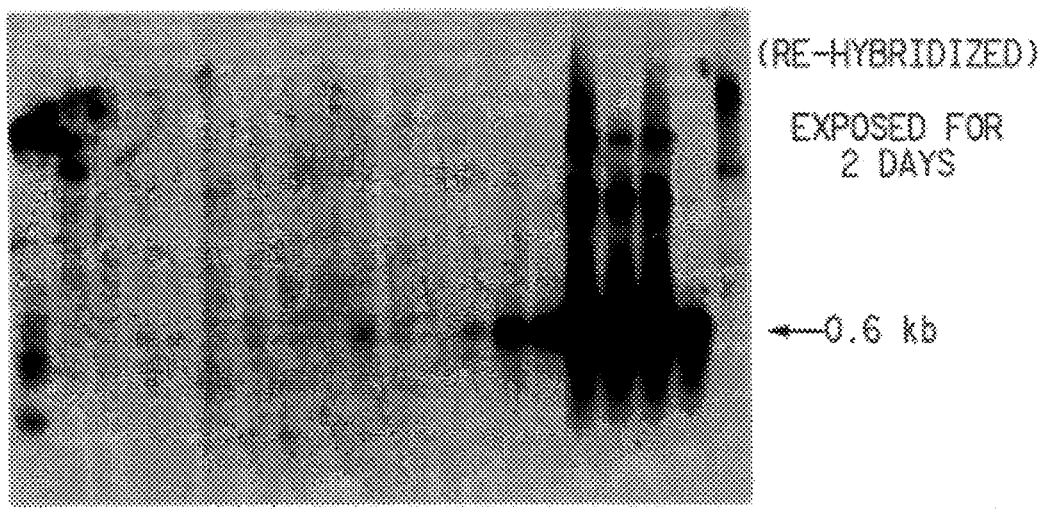

FIG. 6A shows the agarose gel to indicate the amount of total RNA samples loaded in each lane. FIG. 6B is the Northern blot analysis which shows that the gene encoding WM403 was not expressed in the vegetative organs (Lf: leaves, and Rt: roots), not in the male flowers (including An: anthers, and Sp: sepals and petals), nor in the flesh and rind of the developing fruits ($F_1$: young fruits size of 2 cm in length; and $F_2$: fruits size of 10–12 cm in length). The mRNA homologous to clone WM403 started to be detectable in stage 2 ovaries, and accumulated increasingly as the ovary matured. The same blot was re-hybridized with the freshly-made same probe, and over-exposed for two days to reveal any low level of expression (FIG. 6C). A low level of message was detected in the RNA sample extracted from the remaining female floral tissues (lane 10: $T_3$) at the day of anthesis (stage 3), but declined after anthesis (lane 11: $T_4$), and the message was not detected in the RNA samples from these tissues in stage 1 ($T_1$) and 2 ($T_2$). The timing of WM403 expression in the ovule is suitable to induce the excision/activation event by the lox-Cre recombination. However, the low expression in the stigma/style of newly opened flowers, if indeed it is expressed from the same gene, may indicate some effort necessary to screen each individual transformant to find the one with high activity in the nucellus but no or lowest expression in stigma/style.

Determination of DNA sequence of nucellus-specific WM403 cDNA

The WM403 cDNA sequence was determined by sequence analysis of double-stranded plasmid purified using standard procedures (Maniatis et al. 1982). The nucleotide sequence of the WM403 cDNA was determined by the dideoxy method using a $^{T7}$Sequencing™ kit (Pharmacia). The first primers used were the universal and reverse primers. Adjacent regions of the clone were sequenced by priming with synthetic oligonucleotides designed from sequences obtained from previous gel readings. The sequence obtained was used to design primers for primer extension experiments to determine the transcription starting site (see below).

Isolation of nucellus-specific Genomic Clones and Promoters and Construction of Expression Vectors The watermelon genomic DNA was purified from seedlings and leaves, and a genomic library cloned into a Lambda Fix II vector was constructed by Stratagene. The un-amplified library contained $8\times10^6$ independent clones. We have screened $5\times10^5$ clones using the $^{32}$P-labeled WM403 cDNA insert as the probe. Twenty-three putative positive clones corresponding to the WM403 cDNA were obtained from primary screens. Positive clones were confirmed by secondary and tertiary screening. One of them, Lambda 53, containing an insert size of about 6 kb, was chosen for further characterization.

Primer extension and Lambda DNA sequencing by PCR (fmol sequencing kit, Promega) was performed to determine the transcript starting site. The translation starting site (AUG) was found within and close to the 5' end of the cDNA insert. The transcript starting site (+1) was identified at 41 nucleotides (nd) upstream of the AUG. The data indicate that we have a full-length cDNA insert. The transcript size of 0.6 kb determined by Northern blot analysis was consistent with the cDNA size. The same PCR fragments were obtained from using either the genomic DNA or cDNA as the template indicating that there is no intron in this gene. The open reading frame was fully sequenced. It encodes a polypeptide with 116 amino acids (Seq ID.: 2185–2532). No significant homology has been found with other published sequences in the GenBank. There are 173 nd in the 3'-untranslated region of the cDNA insert, which includes a stop codon (UGA) (Seq ID1: 2532–2535), a duplicate polyadenylation signal (AATAA-AATAA) (Seq ID1: 2586–2596 or 2589–2599), and a 21 nd poly(A) tail. The 5'-untranslated region contains only 41 nd (Seq ID1: 2144–2184), and it is AT-rich (68%). A putative TATA box (Seq ID1: 2113–2121) was identified between −23 and −31 upstream of the RNA starting site. The sequence is TATAAATTT, which has only one nucleotide discrepancy from the consensus TATA box (TATAAATTA).

Lambda 53 DNA was partially digested by MboI, and inserted into the compatable BamHI site of the pSK-vector (Stratagene) for easy sequencing and manipulation. One of the transformants, pSKg403-4, containing the entire WM403 cDNA sequence and about 2 kb of upstream sequence was sequenced by Lark Sequencing Technologies Inc. (9545 Katy Fwy, Ste 200, Houston, Tex. 77024-9870). The DNA sequence of upstream regulatory elements, the 5'-untranslated region, WM403 coding region, and 3'-untranslated region is shown in Seq ID1. The 21 nd poly(A) tail was added after nucleotide 2684, and not shown in this genomic DNA sequence. Another transformant, pSKg403-7, contained the same sequence except a shorter upstream region (starting from Seq ID1: 1654, 0.53 kb from the translation starting site). The upstream fragments in both pSKg403-4, and pSKg403-7, were used as promoter sources to construct the expression clones as plasmid and/or binary plasmid forms for transgene expression analysis.

Figure 7:
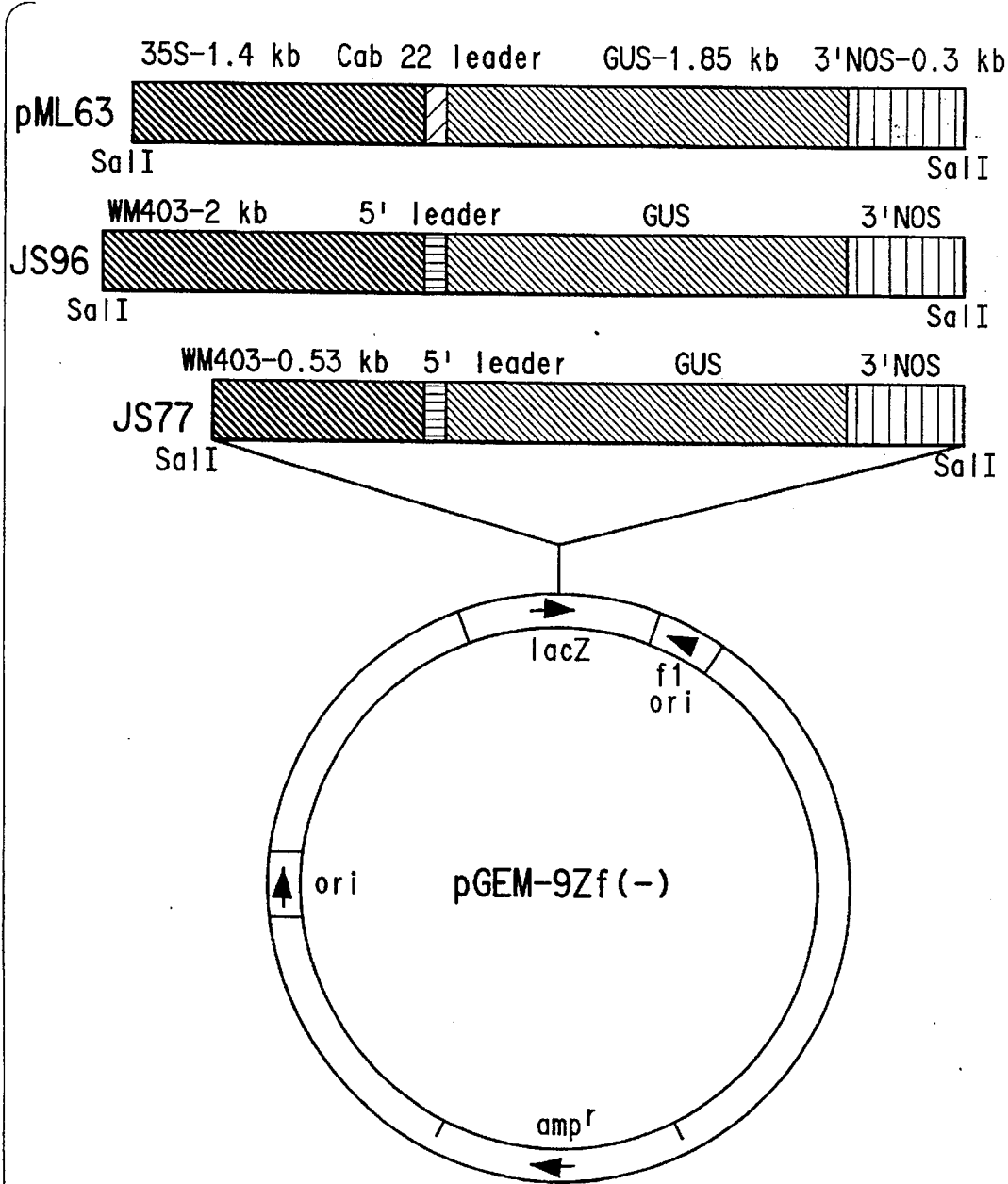
FIG. 7 shows the DNA constructs carrying the GUS reporter gene for the promoter activity assay.

PCR was used to prepare the promoter fragment. The primers were chosen or designed so that the product would have restriction sites available at the fragment ends to ease the subsequent cloning. The primers used in the PCR reaction were T3 (5'-ATTAACCCTCACTAAAG), and WM403-NcoI (5'-CCTTACCGACGATTT-CATGGTCTCTTGC, the underlines indicate the nucleotide differences from the original WM403 cDNA sequence to create an NcoI site). The upstream promoter fragments were amplified by PCR. The resulting product sizes were 0.53 and 2 kb using pSKg403-7, and pSKg403-4 as the templates, respectively. The fragments were then digested with XbaI and NcoI, and ligated with the GUS reporter gene containing the Nos 3'-untranslated region previously inserted into the pGem9Zf(−) vector (Promega), to create expression clones, JS77 and JS96 (FIG. 7). JS77 contained the 0.53 kb promoter that originated from pSKg403-7, and JS96 contained the 2 kb promoter that originated from pSKg403-4. The sequence (41 nd in length) between the transcription starting site (+1) and the translation initiation site (AUG) serves as the 5'-untranslated leader sequence. FIG. 7 shows the plasmid map of the constructs. Note the two nucleotide changes from the original WM403 cDNA at the translation starting junction, which is the result of creating the NcoI site from PCR. pML63 is the expression vector containing the 35S promoter driving the GUS gene, and was used as the constitutive expression control in the transient assay.

Transient Assay of WM403 Promoter

A transient assay using a Biolistic gene gun (DuPont Co.) was used to demonstrate that the upstream fragment from the WM403 coding region possesses promoter activity. Developing watermelon fruit (cv. Oasis) was harvested from the growth chamber at 2–3 weeks post pollination. Immature seeds were collected. Intact seeds, peeled seed coats with the nucellus layer still attached, and embryo sacs, were prepared by dissection under the microscope. The seed tissues were then placed on filter paper on the high osmotic MS medium [Murashige minimal organic medium (MS) 4.6 g/l, Gibco Life Technologies, Gaithersburg, Md., Vitamins B5 0.1%, sucrose 3%, mannitol 9.11%, sorbitol 9.11%, and 0.6% agarose, pH 5.7] to eliminate the excess moisture from the surface, and bombarded with DNA made from the expression clone, JS77.

Seed tissues were examined after bombardment and incubation with X-Glu substrate. Blue spots indicating GUS expression were counted under the microscope. The GUS gene in the positive control, using pML63 (35S: GUS: NOS), was expressed throughout the whole seed section as expected. Whereas the watermelon construct, JS77, showed differential GUS expression in various seed tissues. The most blue spots were observed on the outer seed coat when the intact seeds were bombarded. The expression was also clearly observed in the nucellus layer when the peeled seed coat/nucellus tissues were used for bombardment. There were minimal blue spots in the embryo sac sample. The result indicates that the upstream fragment (only 0.53 kb was used in this experiment) possesses promoter activity in the seed coat and nucellus in the transient assay system. A longer promoter (e.g. 2 kb) may even have higher activity and tighter regulation for tissue specificity.

Transformation and Regeneration

The SalI fragments (FIG. 2) from JS77 and JS96 containing the watermelon nucellus promoter, GUS coding sequence, and NOS 3'-untranslated region, were used to subclone into the SalI site of the binary vector (p535AD with Amp$^r$ marker). The constructs also contained the 35S: tobacco Hra: NOS as the selectable marker. The binary vector was transferred into Agrobacterium tumefaciens (strain LBA4404) by electroporation (BTX electroporation system, San Diego, Calif.).

Watermelon seeds were sterilized, soaked in sterile water overnight, de-coated, and re-sterilized before germinating on medium (MS, 4.6 g/l, 0.8% phytagar, pH 5.7, Gibco Life Technologies, Gaithersburg, Md.) in a dark chamber with temperature maintained at approximately 25° C. Cotyledons were dissected from 4–5 day old seedlings. The meristem tips in conjunction with the cotyledons and hypocotyls were removed. The remaining cotyledon pieces were then inoculated by submerging them for 30 min under vacuum with gentle swirling, in the 10 fold diluted overnight Agrobacterium culture with MS solution (MS 4.6 g/l, pH 5.7). After inoculation, the cotyledon pieces were placed in petri dishes containing the co-cultivation (CoM) medium [MS salt (4.6 g/l), Vitamins B5 0.1%, 3% sucrose, 0.8% phytagar, 0.5 mM Indole-3-Acetic Acid (IAA), and 5 mM 6-Benzylaminopurine (BAP), pH 5.7] for three days in the dark at 24°–25° C. To rid the cotyledon tissues of Agrobacterium and to select for the growth of transformed watermelon cells, the cotyledon tissues were transferred to fresh SIM medium [MS salt (4.6 g/l), Vitamins B5 0.1%, 3% sucrose, 0.8% phytagar, 0.5 mM Indole-3-Acetic Acid (IAA), and 5 mM 6-Benzylaminopurtne (BAP), Glean 50 ppb-100 ppb (W4189, DuPont Co.), Claforan (Cefotaxime, Hoechst-Roussel Pharmaceuticals Inc., Somerville, N.J.) 500 mg/l, pH 5.7]. Among all the media we have tested, the best medium for watermelon regeneration is one containing 5 mM of BAP with or without 0.5 mM of IAA, and the best hormonal combination for muskmelon regeneration is 1 mM of IAA, 5 mM of BAP and 1 mM of ABA. Multiple shoots were induced after three weeks, and elongated by transferring onto fresh SEM medium [MS salt (4.6 g/l), Vitamins B5 0.1%, 3% sucrose, 0.8% phytagar, 0.2 mM Kinetin, Glean 50 ppb-100 ppb, Claforan 500 mg/l, pH 5.7] for another three weeks. The elongated multiple shoots could be separated into single plantlets, and successfully rooted individually on RIM medium [MS salt (4.6 g/l), Vitamins B5 0.1%, 3% sucrose, 0.8% phytagar, 0.1 mM Napthathlene acetic acid, Glean 50 ppb, Claforan 100 mg/1, pH 5.7]. Each node of the regenerated shoot vine was dissected and rooted individually. Acetosyringone (100 mM) can be added to the CoM medium and Agrobacterium cell dilution solution to increase the efficiency of transformation. Other binary vectors can also be used for constructing the plant expression clones. For example, the SalI fragment prepared as described can be inserted into the SalI site of pZS199 which contains Kanr marker, and 35S: Chimeric tobacco Hra: NOS as the selectable marker. Watermelon tissues are transformed as above, except that Carbenicillin (200 mg/L) is used in the selection medium, which is usually more effective to eliminate the growth of Agrobacterium after transformation and less harmful to plant cells than Claforan.

Cre-lox mediated disruption of F2 seed development

The seed maternal tissue-specific promoter is ligated to the barnase coding region followed by the NOS 3' region (or other 3'-polyadenylation signal region from another gene, e.g. the native 3' region of the WM403 gene), creating the chimeric gene called SMTP-bar-NOS 3'.

This chimeric seed maternal tissue SMT for seed maternal tissue disruption gene is made into an inactive form by adding a loxP-polyATloxP DNA fragment between the promoter and coding region as described for the Nos/P-nptII gene in Example 5. The inactive SMTP-lox-bar-NOS 3' gene is cloned into a binary vector between the T-DNA borders along with a chimeric kanamycin resistance selection marker gene. A diagram of the T-DNA of the binary vector is shown below:

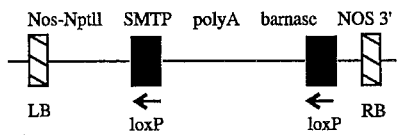

This plasmid, called Lox/SMTPB/NptII, is transferred into A. tumefaciens LBA4404 and the resulting strain is used to obtain watermelon (or other kinds of melon or squash) transformants.

Expression of the cre coding region is more effective either with the same developmentally controlled promoter or with the highly active 35S promoter. The cre coding region is placed under control of the same seed coat/nucellus promoter used for the disruption gene making a chimeric SMTP-Cre-Nos 3' gene. This gene is cloned into a binary vector between the T-DNA borders along with a chimeric hygromycin resistance selection marker gene, creating the SMTPCre/Hpt plasmid. This plasmid is transferred into A. tumefaciens LBA4404 and the resulting strain is used to obtain watermelon (or other kinds of melon or squash) transformants.

Primary transformants containing Lox/SMTPB/NptII are crossed with primary transformants containing SMTPCre/Hpt, and with the homozygous Cre plants (containing the chimetic 35S-Cre gene) described in Section C. Since the primary transformants are heterozygous, the seed produced from their crosses could carry none, both, or either one of the foreign DNA insertions. Therefore, progeny are screened for the presence of the two marker genes, hygromycin and kanamycin resistance. Seeds are germinated on kanamycin, then shoot cuttings are tested for root formation on hygromycin. Progeny resistant to both selections, that therefore carry both the inactive seed maternal tissue disruption gene and the chimeric cre gene, are grown to maturity and selfed. Fruits are checked for the absence of seed indicating that the seed maternal tissue disruption gene is activated by the loxP-cre system thereby disrupting the production of F2 seed.

In crosses of Lox/SMTPB/NptII plants with the homozygous 35S-Cre plants, all progeny receive the chimeric cre gene so only the kanamycin selection is necessary to identify progeny also containing the seed maternal tissue disruption gene. Selected plants are grown to maturity and selfed. Fruits are checked for the absence of seed indicating that the seed maternal tissue disruption gene is activated and effective in disrupting the production of F2 seed.

Homozygous lines of Lox/SMTPB/NptII and of SMTPCre/Hpt plants are obtained as described previously and crossed. Fruits are checked for seed production and seed viability is tested in germination assays. The presence of viable seed indicates that the inactive seed maternal tissue disruption gene maintains its inactive state in the seed maternal tissue of the developing F1 seed as predicted. Progeny are grown to maturity and selfed. Fruits are checked for the absence of seed indicating that the seed maternal tissue disruption gene is activated and effective in disrupting the production of F2 seed. Homozygous Lox/SMTPB/NptII plants are crossed with homozygous 35S-Cre plants and the production of viable F1 seed is tested. Progeny are grown to maturity, selfed, and the absence of F2 seed is observed.

EXAMPLE 15

The watermelon nucellus-specific promoter is embryo and pollen-specific in transgenic tobacco Primary transformants of tobacco containing the watermelon nucellus-specific promoter (WM403-0.53 kb) to express the GUS gene were prepared as described previously and analyzed to study the spatial and developmental regulation of this promoter in this transgenic system. The 35S: Chimeric tobacco Hra: NOS gene was used as the selectable marker.

Among 17 transgenic tobacco plants, four of them were stunted, and no seeds were available at the time of analysis. Tissues from the remaining 13 transformants were hand-sectioned and incubated with X-Glu substrate overnight. The promoter (WM403-0.53 kb) appeared to be regulated both spatially and developmentally. The GUS expression was not detectable in petals, sepals, pistils, seed coats, anther walls, leaves and roots in all transformants. The expression was detected in embryos and pollen, and some of the transgenic plants also showed expression in certain cells in endosperm and stem (in phloem cells and/or pith, but not detectable in epidermal cells, xylem and cortex). Pedicel, although structurally similar to the stem, did not always have the expression as in the stem. The developmental regulation was more obvious in the pollen. Not all stages of the pollen from all transformants were available at the time of analysis, but all the pollen samples examined up to date showed the highest expression at early stages, and expression declined significantly toward maturation. The expression levels in embryo, endosperm, pollen and stem were not always parallel, and the expression in embryo and stem could be uncoupled. Further analysis will be needed to determine if the expression in embryo and young pollen are always linked. The longer upstream regulatory element (WM403-2 kb) may provide a higher promoter activity and tighter tissue specificity. However, this alternate expression of the WM403-0.53 kb promoter in tobacco may provide other utilities for this regulatory sequence.

MEDIA FOR MELON TRANSFORMATION/REGENERATION

GM (Germination Meidum), 50 ml in Plantcon
Per liter:

One package of MS salt (4.6 g) without sucrose
pH 5.7
Phytagar 8 g/L
Vitamin B5 mix (used as 0.1% in the medium)
Per 100 ml

| | |
|---|---|
| Nicotinic acid (Sigma N-0765) | 100 mg |
| Thiamine hydrochloride (Sigma T-3902) | 1 g |
| Pyridoxine hydrochloride (Sigma P0-8666) | 100 mg |
| M-inositol (Sigma I-3011) | 10 g |

CoM (Co-cultivation Medium)
Per liter:

One package of MS salt with sucrose (30 g)
pH 5.7
Vitamin B5 mix 0.1%
Phytagar 8 g/L
After autoclave, add 0.5 µM IAA (0.1 ml of the 5 mM IAA stock)
5 µM BAP (1 ml of the 5 mM BAP stock)
SIM (Shoot Induction Medium)
Per liter:

One package of MS salt with sucrose (30 g)
pH 5.7
Vitamin B5 mix 01.%
Phytagar 8 g/L

MEDIA FOR MELON TRANSFORMATION/REGENERATION

After autoclave, add 0.5 µM IAA (0.1 ml of the 5 mM IAA stock)
5 µM BAP (1 ml of the 5 mM BAP stock in −20° C.
Glean (W4189, 50 ppb)
Claforan (Cefotaxime, 500 mg/L)
SEM (Shoot Elongation Medium)
Per liter:

One package of MS salt with sucrose (30 g)
pH 5.7
Vitamin B5 mix 0.1%
Phytagar 8 g/L
After autoclave, add 0.2 µM kinetin (0.2 ml of the 5 mM kinetin stock)
Glean (W4189, 50 ppb)
Claforan (Cefotaxime, 500 mg/L)
RIM (Root Induction Medium), use platcon
Per liter:

One package of MS salt with sucrose (30 g)
pH 5.7
Vitamin B5 mix 0.1%
Phytagar 8 g/L
After autoclave, add 0.1 µM NAA (0.2 ml of the 5 mM NAA stock per liter)
Glean (W4189, 50 ppb)
Claforan (Cefotaxime, 100 mg/L)

What is claimed is:

1. A method for producing site-specific recombination of DNA in plant cells, comprising:
   i) introducing into the cells a first DNA sequence comprising a first lox site, and a second DNA sequence comprising a second lox site, and
   ii) contacting the lox sites with Cre, thereby producing the site-specific recombination.

2. A method as defined in claim 1, wherein a third DNA sequence comprising a cre coding region is also introduced into the cells.

3. A method as defined in claim 2, wherein the third DNA sequence comprises a promoter that is active in plant cells and expression of the cre gene is produced by direction of the promoter.

4. A method as defined in claim 3, wherein the first and second DNA sequences are introduced into the cells connected by a pre-selected DNA segment.

5. A method as defined in claim 4, wherein the first and second lox sites have the same orientation and the site specific recombination of DNA is a deletion of the pre-selected DNA segment.

6. A method as defined in claim 5, wherein the Cre coding region is obtained from the genome of bacteriophage P1.

7. A method as defined in claim 5, wherein the first and second lox sites are comprised of loxP sites.

8. A method as defined in claim 5, wherein the first and second lox sites are loxP.

9. A method as defined in claim 5, wherein the pre-selected DNA segment is selected from the group consisting of a gene, a coding region, and a DNA sequence that regulates gene expression in plant cells.

10. A method as defined in claim 5, wherein the pre-selected DNA segment is an undesired marker or trait gene.

11. A method as defined in claim 4, wherein the first and second lox sites have opposite orientations and the site-specific recombination is an inversion of the nucleotide sequence of the pre-selected DNA segment.

12. A method as defined in claim 11, wherein the Cre coding region is obtained from the genome of bacteriophage P1.

13. A method as defined in claim 12, wherein the first and second lox sites are comprised of loxP sites.

14. A method as defined in claim 12, wherein the first and second lox sites are loxP.

15. A method as defined in claim 11, wherein the pre-selected DNA segment is selected from the group consisting of a gene, a coding region, and a DNA sequence that regulates gene expression in plant cells.

16. A method as defined in claim 1, wherein the first and second DNA sequences are introduced into two different DNA molecules and the site-specific recombination is a reciprocal exchange of DNA segments proximate to the lox sites.

17. A method as defined in claim 16, wherein the cre coding region is obtained from the genome of bacteriophage P1.

18. A method as defined in claim 17, wherein the first and second lox sites are comprised of loxP sites.

19. A method as defined in claim 17, wherein the first and second lox sites are loxP.

20. A method of excising exogenous genes or DNA segments in transgenic plants, comprising:
   i) introducing into the cells a DNA sequence comprising a first lox site, a second lox site in the same orientation as the first lox site, and a gene or a DNA sequence there between, and
   ii) contacting the lox sites with Cre, thereby excising the heterologous gene or DNA sequence.

21. A method as defined in claim 20, wherein the gene is an undesired marker or trait gene.

22. A plant cell transformed with a DNA sequence comprising at least one lox site.

23. A plant cell containing Cre protein.

24. A plant cell transformed with a cre coding region.

25. A plant containing cells transformed with a DNA sequence comprising at least one lox site.

26. A plant of claim 25 wherein the DNA sequence comprises two lox sites and a cre coding region.

27. A plant containing cells transformed with a cre coding region.

28. A plasmid having at least one lox site and a pre-selected DNA segment selected from the group consisting of a gene, a coding region and a DNA sequence that regulates gene expression in plant cells, said pre-selected DNA segment located proximate to said lox site.

29. A plasmid as defined in claim 28, wherein the DNA sequence is a polyadenylation nucleotide sequence derived from the Rubisco small subunit gene.

30. A plasmid as defined in claim 28, wherein the DNA segment is a gene encoding a product selected from the group consisting of an antisense RNA, a ribozyme, an enzyme, a structural protein, and a selection marker.

31. A plasmid as defined in claim 28, wherein the DNA sequence is a promoter.

32. A plasmid as defined in claim 28, wherein the DNA sequence is a 5' or 3' regulatory nucleotide sequence.

33. Plasmid Cre/Hpt-A which corresponds to the restriction enzyme map shown in FIG. 1A and which is deposited as ATCC accession number ATCC 68176.

34. Plasmid Cre/Hpt-B which corresponds to the restriction enzyme map shown in FIG. 1B, and which is deposited as ATCC accession number ATCC 68175.

35. Plasmid pZ4loxAG which corresponds to the restriction enzyme map shown in FIG. 4, and which is deposited as ATCC accession number ATCC 97665.

36. A plasmid having a Cre coding region and a promoter that is active in plant cells wherein expression of the Cre coding region is under the direction of said promoter.

37. A DNA sequence comprising at least one lox site and a pre-selected DNA segment selected from the group consisting of a gene, a coding region and a DNA sequence that regulates gene expression in plant cells, said pre-selected DNA segment located proximate to said lox site.

38. A DNA sequence comprising a Cre coding region and a promoter that is active in plant cells wherein expression of the Cre coding region is under the direction of said promoter.

39. Plasmid loxP/NptII/Hra which corresponds to the restriction enzyme map shown in FIG. 1C, and which is deposited as ATCC accession number ATCC 68177.

* * * * *

UNITED STATES PATENT AND TRADEMARK OFFICE
CERTIFICATE OF CORRECTION

PATENT NO. : 5,658,772
DATED : August 19, 1997
INVENTOR(S) : Joan Tellefson Odell et al.

It is certified that error appears in the above-identified patent and that said Letters Patent is hereby corrected as shown below:

In Column 2, line 51, please delete "DNA sequence comprising at least one lox site, or with acre" and replace with the following: --DNA sequence comprising at least one lox site, or with a cre--.

In Column 2, line 53, please delete "as a plant containing cells transformed with acre coding" and replace with the following: --as a plant containing cells transformed with a cre coding--.

Signed and Sealed this

Third Day of February, 1998

Attest:

BRUCE LEHMAN

*Attesting Officer*    *Commissioner of Patents and Trademarks*